US006030609A

United States Patent [19]

Panuska et al.

[11] Patent Number: 6,030,609

[45] **Date of Patent: *Feb. 29, 2000**

[54] METHOD AND COMPOSITION FOR TREATING PARAMYXOVIRUS

[75] Inventors: James R. Panuska, Shaker Heights; Nick M. Cirino, Cleveland, both of Ohio

[73] Assignee: Case Western Reserve University, Cleveland, Ohio

[ * ] Notice: This patent is subject to a terminal disclaimer.

[21] Appl. No.: 08/444,256

[22] Filed: May 19, 1995

[51] Int. Cl.$^7$ ........................ C07K 14/52; C07K 14/555; A61K 38/19; A61K 38/21

[52] U.S. Cl. .................... 424/85.6; 424/85.4; 435/69.51; 435/243; 435/235.1

[58] Field of Search ........................... 424/85.6; 435/243, 435/235.1, 69.51

[56] References Cited

PUBLICATIONS

Sperber S.J., Comparative susceptibility of Respiratory Viruses to Recombinant interferon–$\alpha_{2b}$ and –β; Journal of Interferon Research 9: 285–293 (1989).

Merigan et al., Inhibition of Respiratory Virus Infection By Locally Applied Interferon; The Lancet, Saturday Mar. 17, 1973; 563–567.

Merolla et al.; Respiratory Syncytial Virus Replication In Human Lung Epithelial Cells:Inhibition By Tumor Necrosis Factor α and Interferon β; Am. J. Respir. Crit. Care Med. vol. 152, pp. 1358–1366, 1995.

*Primary Examiner*—Cecilia Tsang
*Assistant Examiner*—Michael Borin
*Attorney, Agent, or Firm*—Fay, Sharpe, Beall, Fagan, Minnich & McKee

[57] ABSTRACT

The present invention relates to a method of treating respiratory syncytial virus (RSV) through the exogenous administration of recombinant or natural interferon-beta (IFN-β) to lung epithelial cells. Preferably, IFN-β is administered to hosts suffering from RSV in effective nebulized or aerosolized doses.

16 Claims, 13 Drawing Sheets

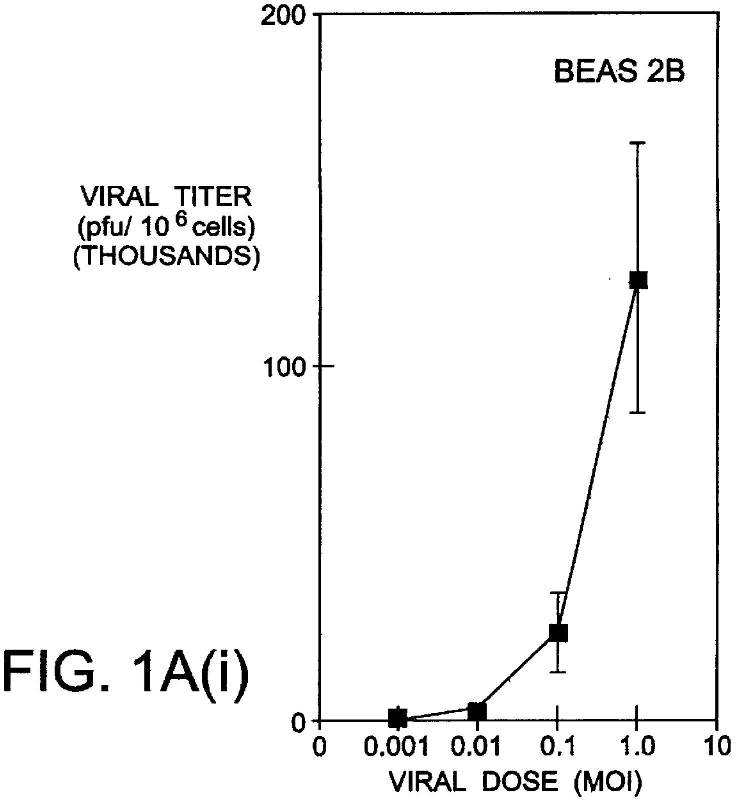
FIG. 1A(i)
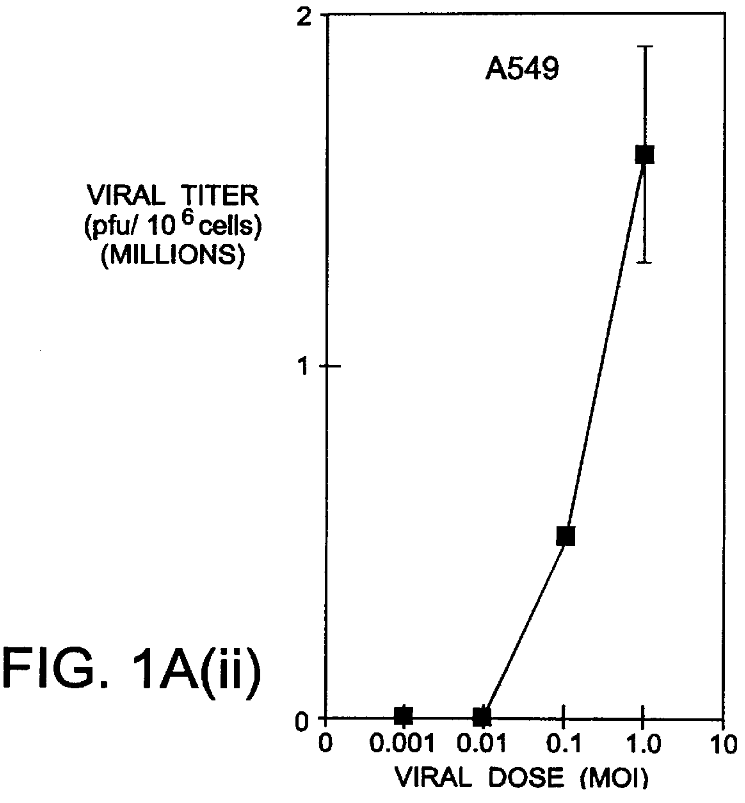
FIG. 1A(ii)

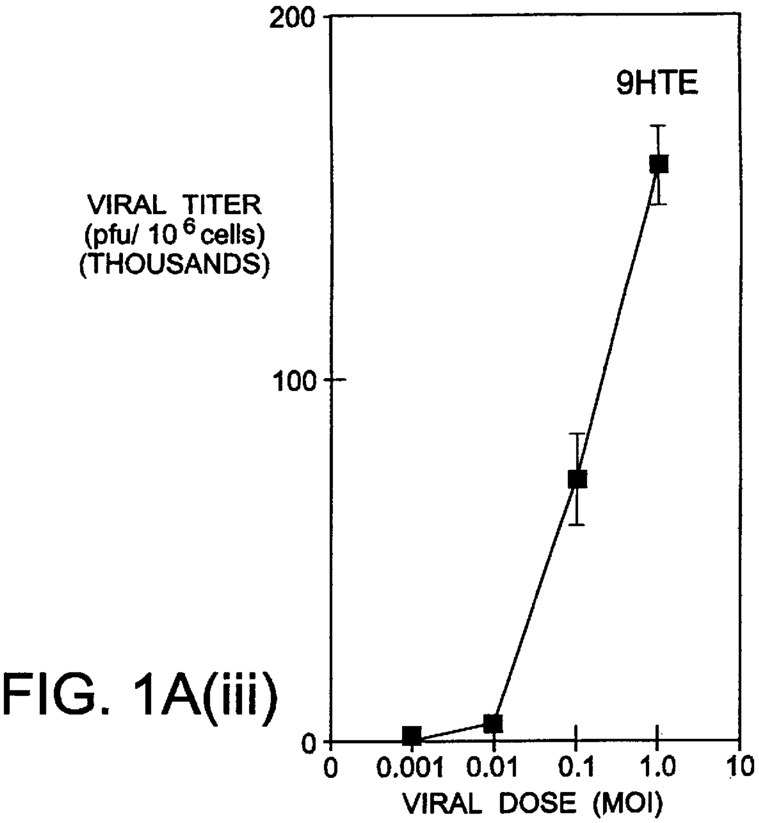
FIG. 1A(iii)
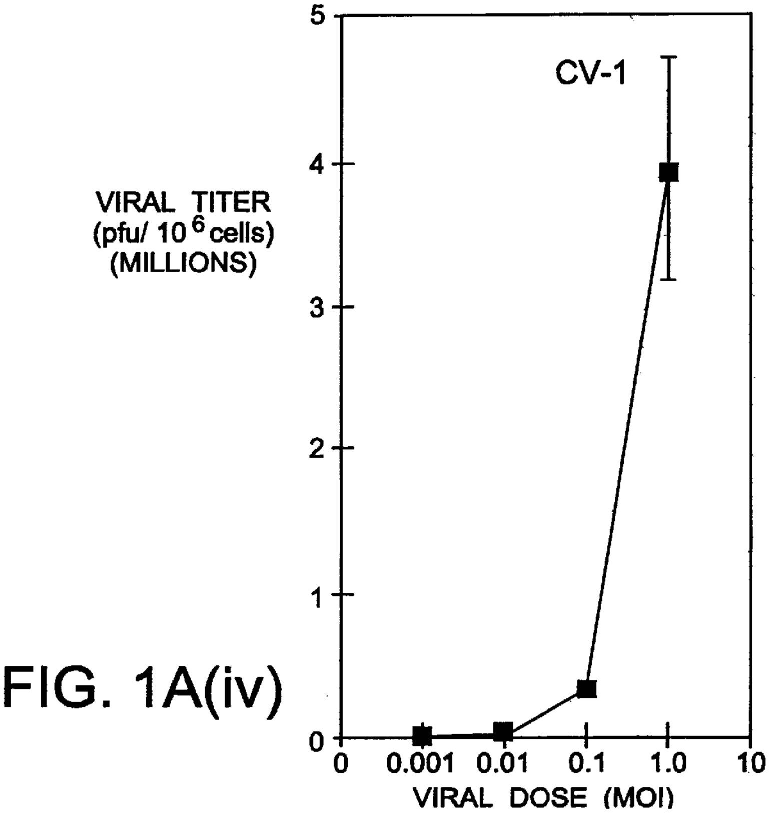
FIG. 1A(iv)

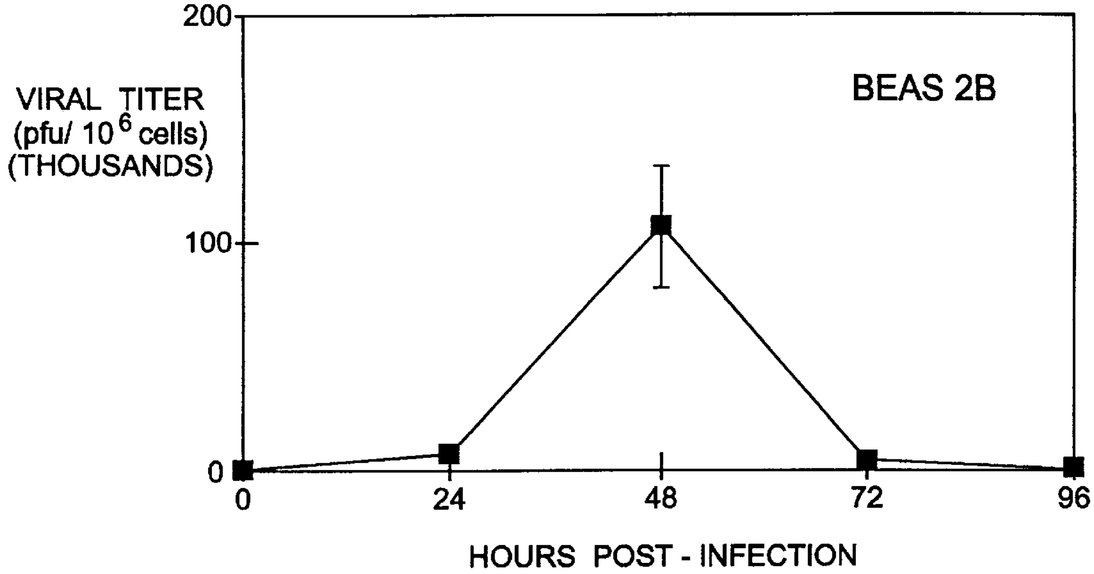
FIG. 1B(i)
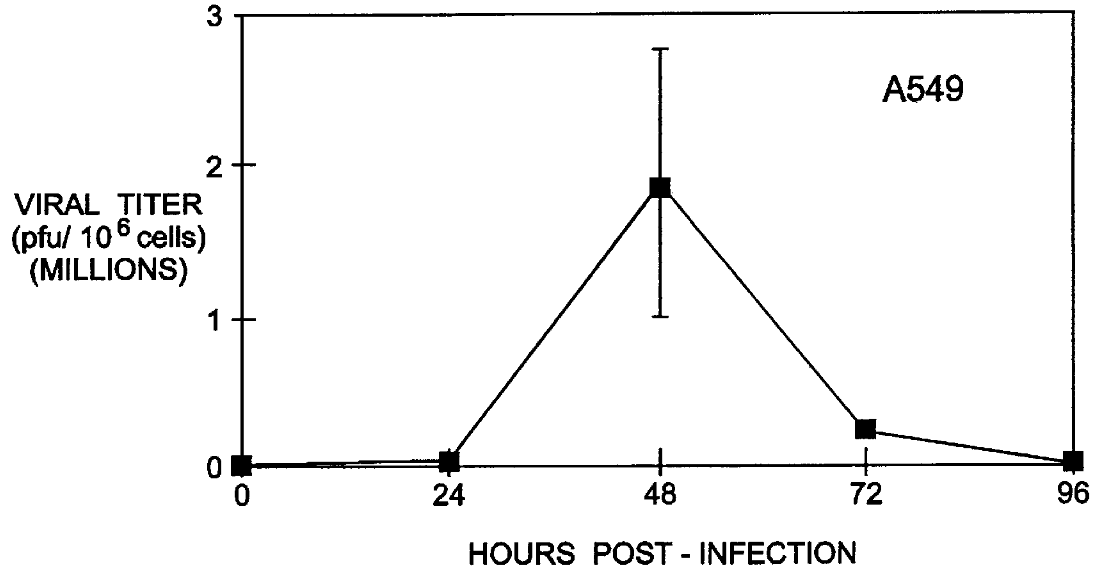
FIG. 1B(ii)

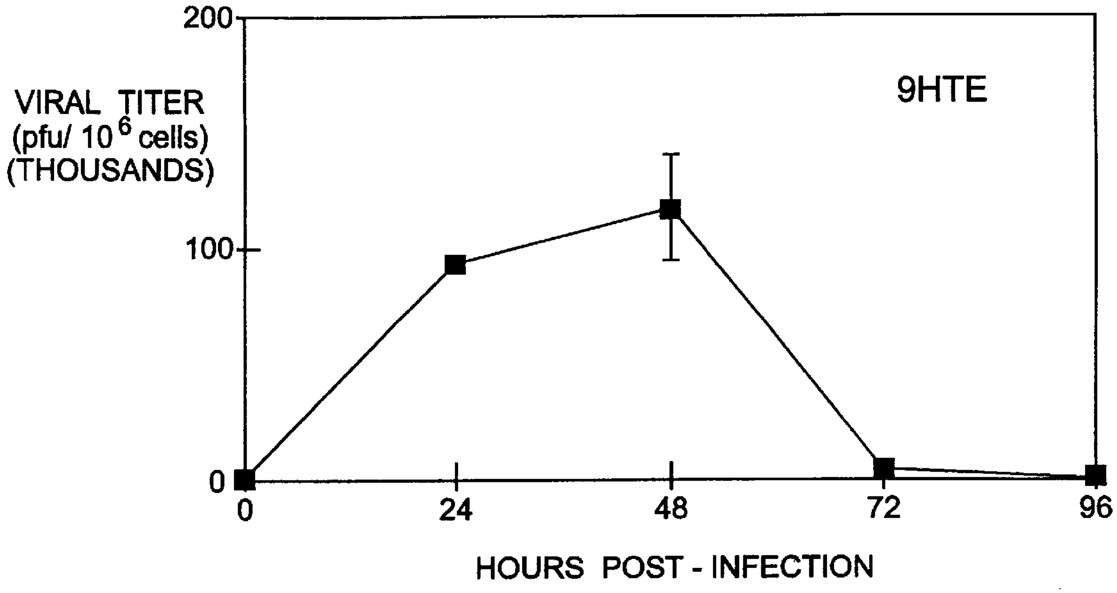
FIG. 1B(iii)
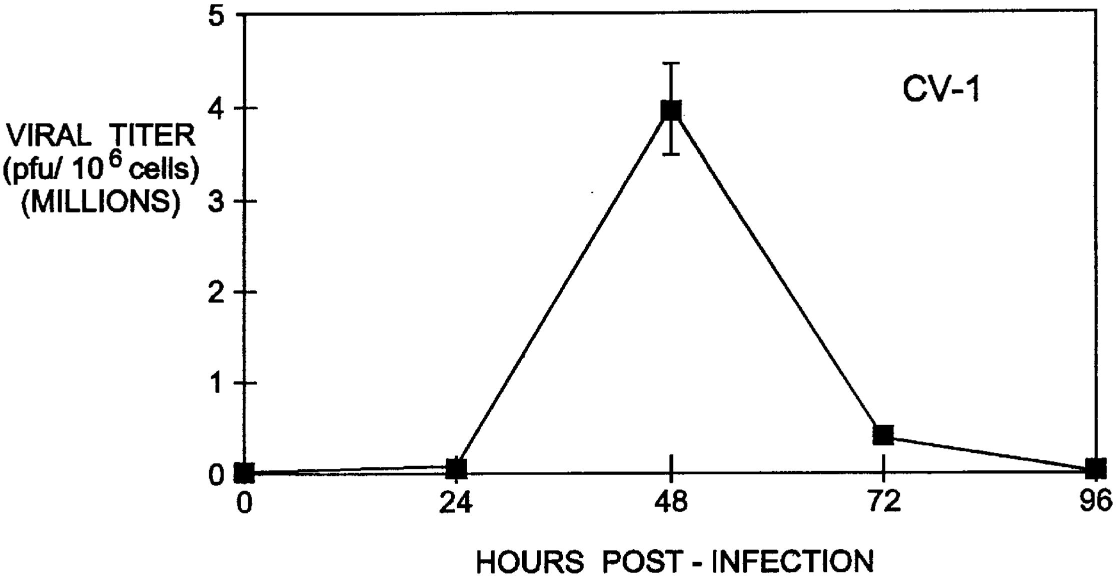
FIG. 1B(iv)

METHOD AND COMPOSITION FOR TREATING PARAMYXOVIRUS

FIELD OF THE INVENTION

The present invention is directed to a method of treating respiratory diseases caused by respiratory syncytial virus (RSV) through the exogenous administration of recombinant or natural interferon-beta (IFN-β). More particularly, the invention relates to methods for treating RSV through the administration of an effective amount of IFN-β to resident lung cells (e.g. macrophages, epithelial, etc.) to reduce RSV replication and/or to prevent infection of adjacent cells. Preferably the IFN-β is administered through nebulization. The nebulized compound is inhaled by the patient so as to activate lung cells to interfere with virus replication. It has been found that IFN-β interacts with appropriate receptors on epithelial cells in mammals to restrict RSV replication. The invention also provides pharmaceutical compositions suitable for inhalation and for the purposes indicated above.

BACKGROUND OF THE INVENTION

Paramyxoviruses comprise a family of RNA viruses tropic for the human respiratory tract, that result in approximately 13 million infections per year. RSV, a major pathogen within the Paramyxovirus family, causes severe lung disease in young children, elderly adults, and immunocompromised individuals. To date, no effective vaccine for RSV presently exists despite the estimated 1 million deaths this virus causes annually in infants and children.

It has been found that most infected older children and adults restrict and eliminate RSV rapidly. However, young infants and children are susceptible to infection of bronchiolar and alveolar cells resulting in bronchiolitis, pneumonia or respiratory compromise which may result in death. Symptoms such as nasal discharge, fever, fatigue, deep cough, wheezing and shortness of breath are generally associated with RSV infections. Reinfections are common, especially in infants and young children.

Structurally, RSV is an enveloped, negative stranded RNA virus of the family Paramyxoviridae and of the genus pneumovirus. The two major envelope proteins are the G protein, which is believed to be responsible for attachment of the virus to the host cell membrane, and the fusion (F) protein, which is believed to be responsible for fusing the virus and cell membranes. Virus-cell fusion is a necessary step for infection. F protein is required for cell-cell fusion which is another way to spread the virus from an infected cell to an adjacent uninfected cell. Antibodies directed against these proteins do not confer significant immunity in humans.

The targets for RSV infections are generally the terminal bronchioles and alveoli in mammals which are lined by lung epithelial cells and alveolar macrophages. If these cells permit unrestricted RSV replication, viral burden progressively increases resulting in denudation of the airway and destruction of alveolar macrophages which defend the lung against other pathogens.

It has been found that most children can recover from RSV infection indicating that they can eliminate RSV. This implies that intrinsic cellular mechanisms, as yet undefined, may restrict virus replication. However, the reason why some children have progressive disease that can culminate in overwhelming infection and death is not yet known.

Although RSV has been extensively studied, there are no available effective vaccines to combat RSV. The lack of an effective vaccine for RSV suggests that strategies to augment intrinsic lung defenses against this virus could offer potential clinical benefits. Therefore, applicants examined whether differentiated human lung epithelial cells possess intrinsic mechanisms to restrict RSV replication, whether such intrinsic mechanisms could be augmented by anti-viral cytokines (e.g. IFN-β), and whether anti-viral cytokines could be operative before induction of humoral or cell-mediated immune responses.

In this regard, applicants studied RSV replication in normal human lung epithelial cells transformed with an origin defective SV-40 vector, i.e. 9HTE (tracheal origin) and BEAS 2B cells (bronchiolar origin). In addition, applicants examined the non-transformed human A549 cells (alveolar epithelial origin) derived from an alveolar carcinoma. These differentiated lung epithelial cell lines offer an in vitro model with which insights into the molecular mechanisms that restrict RSV in human lung cells can be examined. In addition, the differentiated lung epithelial cell lines offer advantages over highly permissive cell lines, such as CV-1, HEp-2 cells, or HeLa cells, which lack characteristics of differentiated human lung cells.

Moreover, it is believed that alveolar macrophages may have an important role in restricting replication of respiratory viruses through their capacity to produce tumor necrosis factor a (hereafter referred to as TNFα). Local production of TNFα at the site of virus infection has previously been shown to restrict vaccinia virus replication (Sambhi, S.K., Kohonen-Corish, M. R. J., and L. A. Ramshaw. 1991. Local production of tumor necrosis factor encoded by recombinant vaccinia virus is effective in controlling viral replication in vivo. *Proc Natl Acad Sci*. 88:40254029). In vitro and in vivo studies have demonstrated that alveolar macrophages are permissive to RSV infection/replication and produce TNFα following RSV infection (Panuska, J. R., Hertz, M. 1., Taraf, H., Villani, A., and N. M. Cirino. 1992. Respiratory syncytial virus infection of alveolar macrophages in adult transplant patients. *Am. Rev. Respir. Dis*. 145:934939).

Furthermore, it has been determined that TNFα restricts further RSV replication in alveolar macrophages through an autocrine mechanism. The intimate contact between alveolar macrophages and epithelial cells from terminal bronchioles and alveoli suggests that TNFα could potentially restrict RSV through paracrine mechanisms. However, the potential use of recombinant TNFα as a systemic antival therapy is limited by its toxicity.

Applicants therefore examined whether RSV could be transmitted between lung epithelial cells and alveolar macrophages. Applicants further examined TNFα binding to lung epithelial and CV-1 cells and whether these separate cell types expressed the 55 and 75 kDa TNFα receptor subtypes (Loetscher, H., Pan, Y. E., Lahm, H., Gentz, R., Brockhaus, M., Tabuchi, H., and W. Lesslauer. 1990. Molecular cloning and expression of the human 55 kd tumor necrosis factor receptor. *Cell* 61:351–359; Pennica, D., Lam, V. T., Mize, N. K., Weber, R. F., Lewis, M., Fendly, B. M., Lipari, M. T., and D. V. Goeddel. 1992. Biochemical properties of the 75-kDa tumor necrosis factor receptor. *J. Biol Chem*. 267:21172–211 78). The 55 kDa TNFα receptor mediates the anti-viral effects of TNFα in some (Wong, G. H. W., Tartaglia, L. A., Lee, M. S., and D. V. Goeddel. 1992. Antiviral activity of tumor necrosis factor (TNFα) is signaled through the 55-kDa receptor, type 1 TNF*J. Immunology* 149:3350–3353), but not all cell types (Rothe, J., Lesslauer, W., Lotsher, H., Land, Y., Koebel, P., Kontgen, F., Althage, A., Zinkernagel, R., Steinmetz, M., and H. Bluethmann. 1993; Mice lacking the tumor necrosis factor receptor 1 are resistant to TNF mediated toxicity but highly susceptible to infection by *Listeria monocytogenes*. *Nature* 364:798–802).

In this regard, it is known to some degree that TNFα and IFN-β, individually, or synergistically, can restrict replication of both RNA and DNA viruses (Sen, G. C., and R. M. Ransohoff. 1993. Interferon-induced antiviral actions and their regulation. *Adv. Virus Res*. 42:57–101; Wong, G. H. W., Kamb, A., and D. V. Goeddel 1993. Antiviral properties of TNF. In B. Beutler, editor. Tumor Necrosis Factors: The Molecules and Their Emerging Role in Medicine.Raven Press. Ltd, New York, 371–381). IFN restricts RSV replication in lung fibroblast cell lines (Moehring, J. M., and B. R. Forsyth. 1971. The role of the interferon system in respiratory syncytial virus infections. *Proc Soc Exp. Biol Med*.138:1009–1014) but its effects on RSV replication in lung epithelial cells had not been previously examined. RSV induces low levels of IFN in only ~50% of infected children (Hall, C. B., Douglas, R. G. Jr, Simons, R. L., and J. M. Geiman.1978. Interferon production in children with respiratory syncytial, influenza, and parainfluenza virus infections. *J. Pediatr*. 93:28–32) and does not induce IFN expression from macrophages in vitro (Roberts, N. J. Jr, Hiscon, J., and D. J. Signs. 1992. The limited role of the interferon system in response to respiratory syncytial virus challenge: analysis and comparison to influenza virus challenge. *Microbial Pathogenesis*.12:409414).

The Applicants have shown that RSV potently induces the cytokine surpressing inhibitor factor, termed IL-10, by infected human macrophages and epithelial cells which directly inhibits IFN production. (Hoffmann, S. P., Rebert, N. A., Panuska, J. R. 1995. Respiratory Syncytial Virus Induction of Lung Cell Expression of Interleukin 10: Implications For Incomplete Immunity. *Am. J. of Resp. and Crit. Care Medicine* 151:A774). Thus, RSV inhibits expression of anti-viral cytokines by resident lung cells.

However, IFN treatment of RSV infected children does improve their clinical course suggesting that exogenous IFN may augment intrinsic lung defenses against this virus (Sung, R. Y. T., Yin, J., Oppenheimer, S. J., Tam, J. S., and J. Lau. 1993. Treatment of respiratory syncytial virus infection with recombinant interferon alfa-2a. *Arch Dis. Child* 69:440–442).

Applicants therefore determined the effects of TNFα and IFN-β alone, and in combination, on RSV infection and replication in lung epithelial cells as well as the highly RSV permissive CV-1 cell line. Moreover, applicants examined known mechanisms by which TNFα and/or IFN-β restrict virus replication including inhibition of virus infection, cytostatic effects on cells, direct lysis of virus infected cells, or inhibition of protein synthesis which reflects induction of TNFα/IFN-β responsive anti-viral genes.

As shown below, applicants have found that IFN-β restricts RSV replication in human lung epithelial cells, the natural target cells for this virus. Previously, delivery of ribavirin (1-beta-D-ribofuranosyl-1-1, 2, 4-triazole-3-carboxamide), a synthetic nucleotide that is administered intravenously by small particle aerosol for 12–20 h a day for approximately three (3) days was essentially the only anti-viral drug and/or treatment useful in RSV infections. However, ribavirin's clinical efficacy has been marginal and its potential teratogenic effects have limited its use. Nevertheless, it is used in ~20,000 children per year at a cost of $3,000 per patient.

The present invention relates to the specific delivery of IFN-β to the airway of a host susceptible or suffering from infection of RSV and other RNA respiratory viruses. Recent studies have indicated that INF-β can be delivered by aerosol to volunteers without causing any harmful effects. (Halme, M., Maasilta, P., Mattson, K., Cantell, K. 1994. Pharmacokinetics and Toxicity of Inhaled Human Natural Interferon-Beta in Patients With Lung Cancer. *Respiration* 61:105–107). The invention has the ability to restrict RSV without inducing side effects that can be observed with parenterally administered IFN-β. It also has the potential to restrict other RNA viruses which might be sensitive to cytokines.

These and other objects of the present invention will be more apparent from the discussion below.

SUMMARY OF THE INVENTION

In one aspect, the present invention relates to a method of treating respiratory syncytial virus (RSV) through the exogenous administration of recombinant or natural interferon-beta (IFN-β) to lung epithelial cells. Preferably, IFN-β is administered to hosts suffering from RSV as an effective nebulized or aerosolized form.

Along these lines, it has been found through the study of lung epithelial cell lines exposed to RSV that virus replication proceeds in a dose and time dependent manner. In addition, it has been found that the administration of exogenous tumor necrosis factor (TNFα) and/or interferon-beta (INF-β) markedly inhibits RSV in a similar manner.

Specifically, it has been determined that exogenous interferon-beta (INF-β) essentially aborts RSV replication in human lung epithelial cells. Moreover, IFN-β and/or TNFα did not induce cell membrane damage, cause cell lysis, nor inhibit cellular protein synthesis. RSV infected human alveolar macrophages, which produce TNFα, failed to productively infect lung epithelial cells in co-culture. Together these results indicate that endogenous TNFα coupled with exogenous IFN-β can overcome the deficient IFN expression by lung cells to yield restricted RSV replication. Consequently, the present invention is directed to a method of treating virus induced respiratory diseases such as RSV through the use of IFN-β.

In a further aspect, the present invention relates to pharmaceutical compositions suitable for use in the treatment of RSV and potentially other paramyxovirus via inhalation. The pharmaceutical compositions contain as the active ingredient, an effective amount of recombinant or natural IFN-β. In addition, one or more carriers, stabilizers, surfactants, buffers, anti-inflammatory agents, antibiotics, may be included in the pharmaceutical compositions in order to enhance the effectiveness or delivery efficiency of the active agent.

These and other objects and features of the invention will be apparent from the following drawings, detailed description of the invention and from the claims. It should, however, be understood that the detailed description and the specific examples, while indicating preferred embodiments of the invention, are given by way of illustration only, since various modifications and changes within the spirit and scope of the invention will become apparent to those skilled in the art.

BRIEF DESCRIPTION OF THE DRAWINGS

The following is a brief description of the drawings which are presented for the purpose of illustrating the invention and not for the purpose of limiting same.

FIGS. 1A(i)–1A(iv) show the production of infectious RSV as a function of viral dose. Lung epithelial and CV-1 cells, as indicated, were exposed to the indicated doses of RSV and total virus titer (sonicated cells+supernatants)/$10^6$ cells were determined at 48 h p.i. Results shown are mean±SEM, n=5. Virus titer is shown as thousands for BEAS 2B and 9HTE cells and millions for A549 and CV-1 cells in this, and subsequent Figures. The increase in virus titer in all cells exposed to RSV>0.1 pfu/cell was significant at P<0.01, ANOVA.

FIGS 1B(i)–1B(iv) show the production of RSV as a function of time following infection (MOI=1). Total RSV production/$10^6$ cells was determined at the indicated h p.i. Results shown are mean±SEM, n=5. RSV titer was significantly higher at 48 h in all cell types compared to other time points, P<0.01, Student's t-tests.

FIGS. 2A–2D demonstrate the effects of TNFα on RSV production by lung epithelial and CV-1 cells. Cells were treated with TNFα at the indicated doses for 16 hours, then exposed to RSV at 1 pfu/cell. After washing, cell monolayers were incubated in fresh media for 48 hours and viral titer was determined as described in the Examples. Results shown are mean±SEM, n=5. Asterisks indicate significant (P<0.05) differences compared to untreated controls by Student's t-tests.

Figure 2A:
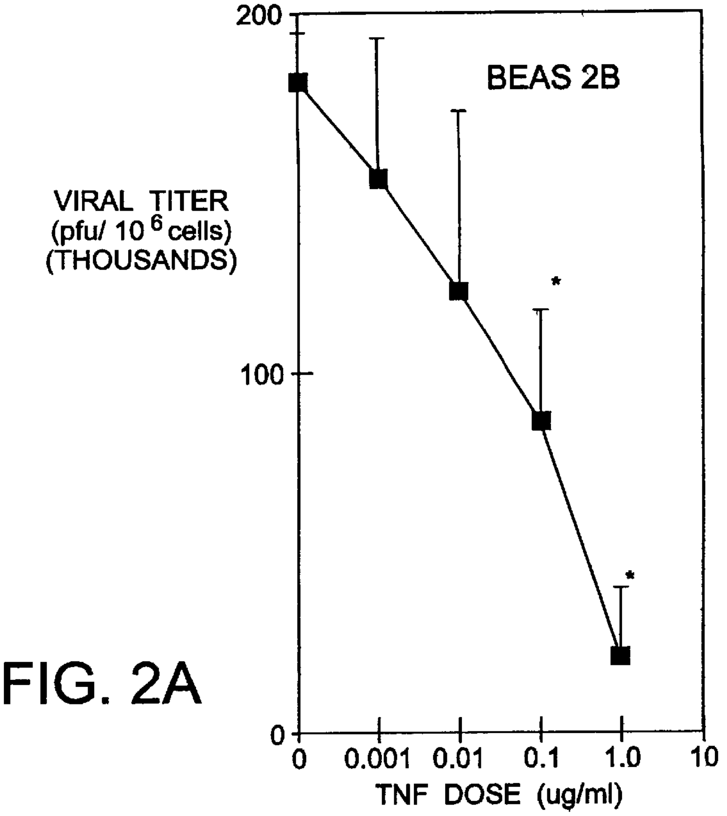
Figure 2B:
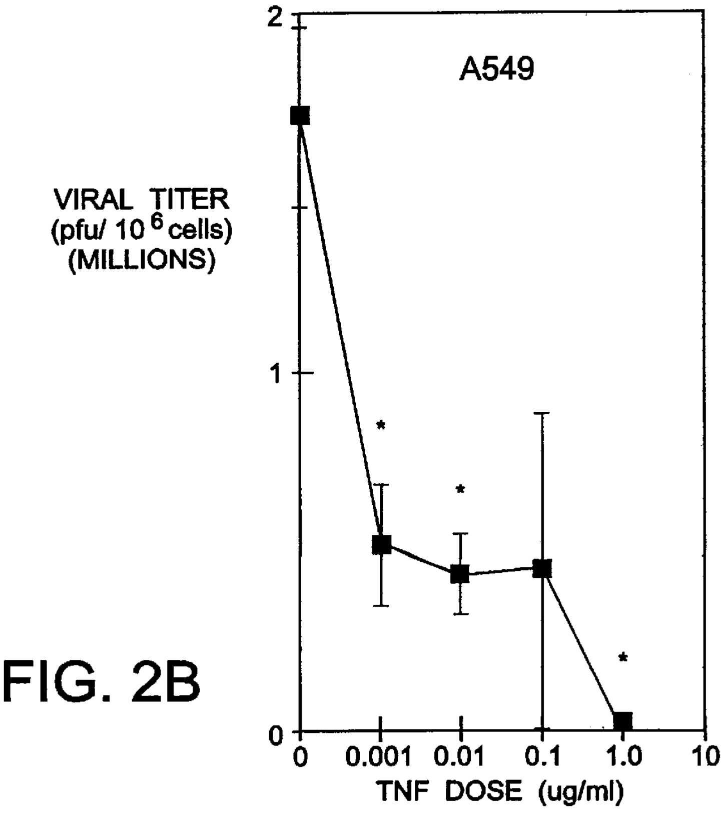
Figure 2C:
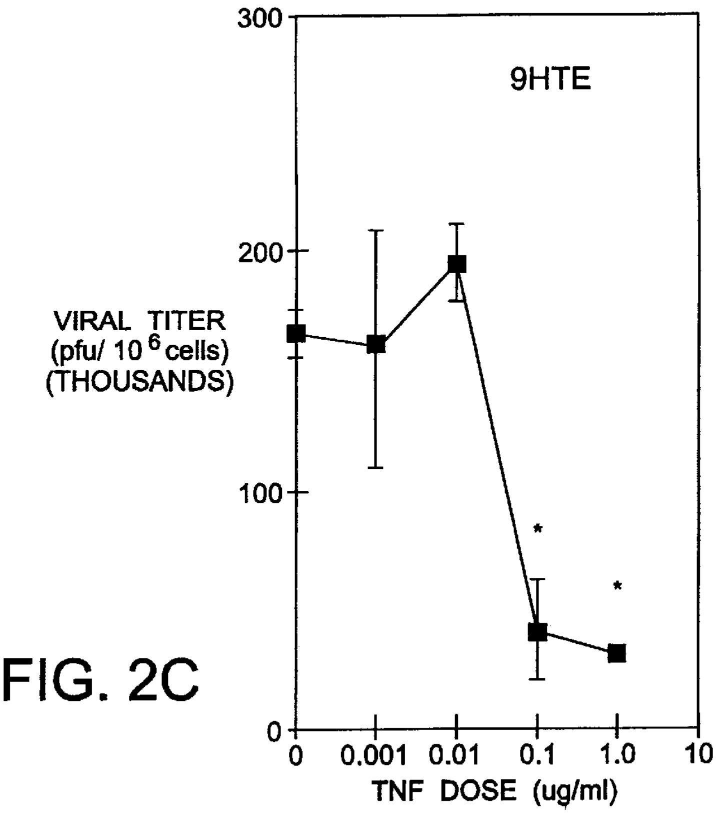
Figure 2D:
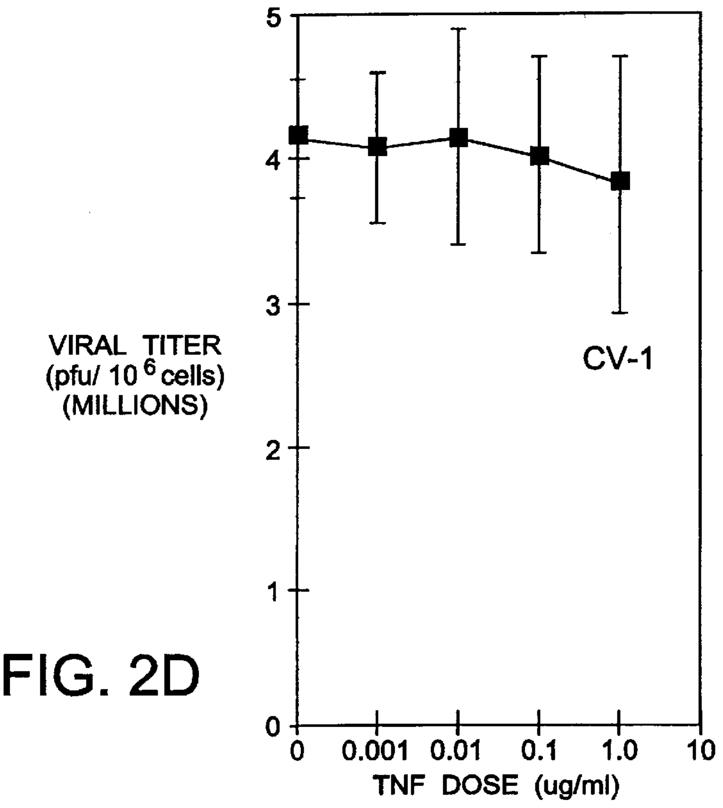
Figure 3A:
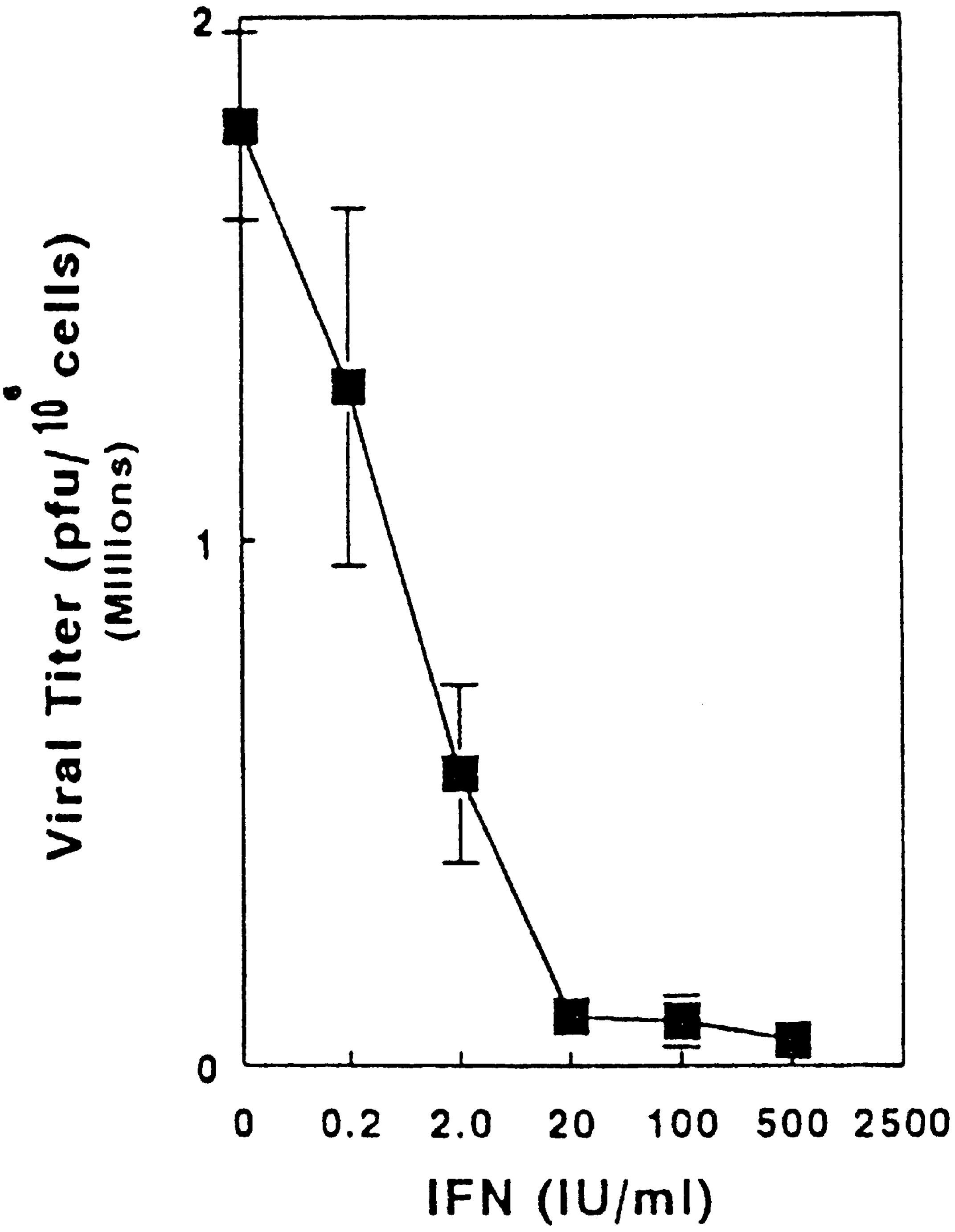

FIG. 3A indicates the effects of IFN-β on RSV replication in A549 cells. A549 cells were exposed to IFN-β at the indicated doses for 16 hours then infected with RSV (MOI=1). After 48 hours, total RSV production (sonicated cells+supernatants) was determined as described in the Examples. Results shown are mean+SEM, n=4. Doses greater than 2 IU/ml were significantly (P<0.01) less than controls.

Figure 3B:
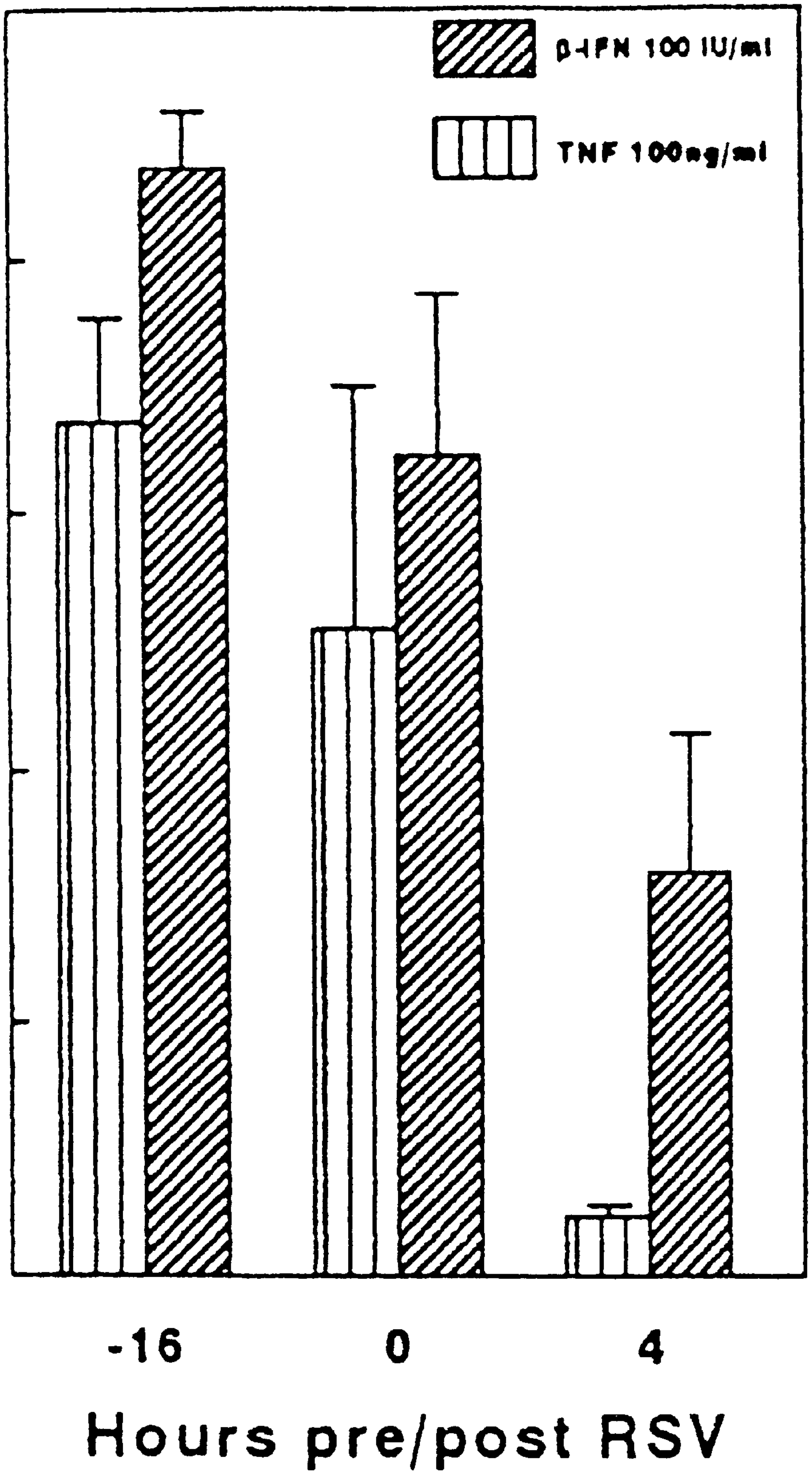

FIG. 3B indicates the effects of TNFα (100 ng/ml) and IFN-β (100 IU/ml) on RSV replication in A549 cells following infection with an MOI=1. A549 cells were pretreated (−16 hours), treated simultaneously (0 hours), or post-treated (4 hours) as indicated with TNFα or IFN-β and the reduction in RSV production was determined compared to untreated cultures. Results are mean±SEM, n=4.

Figure 3C:
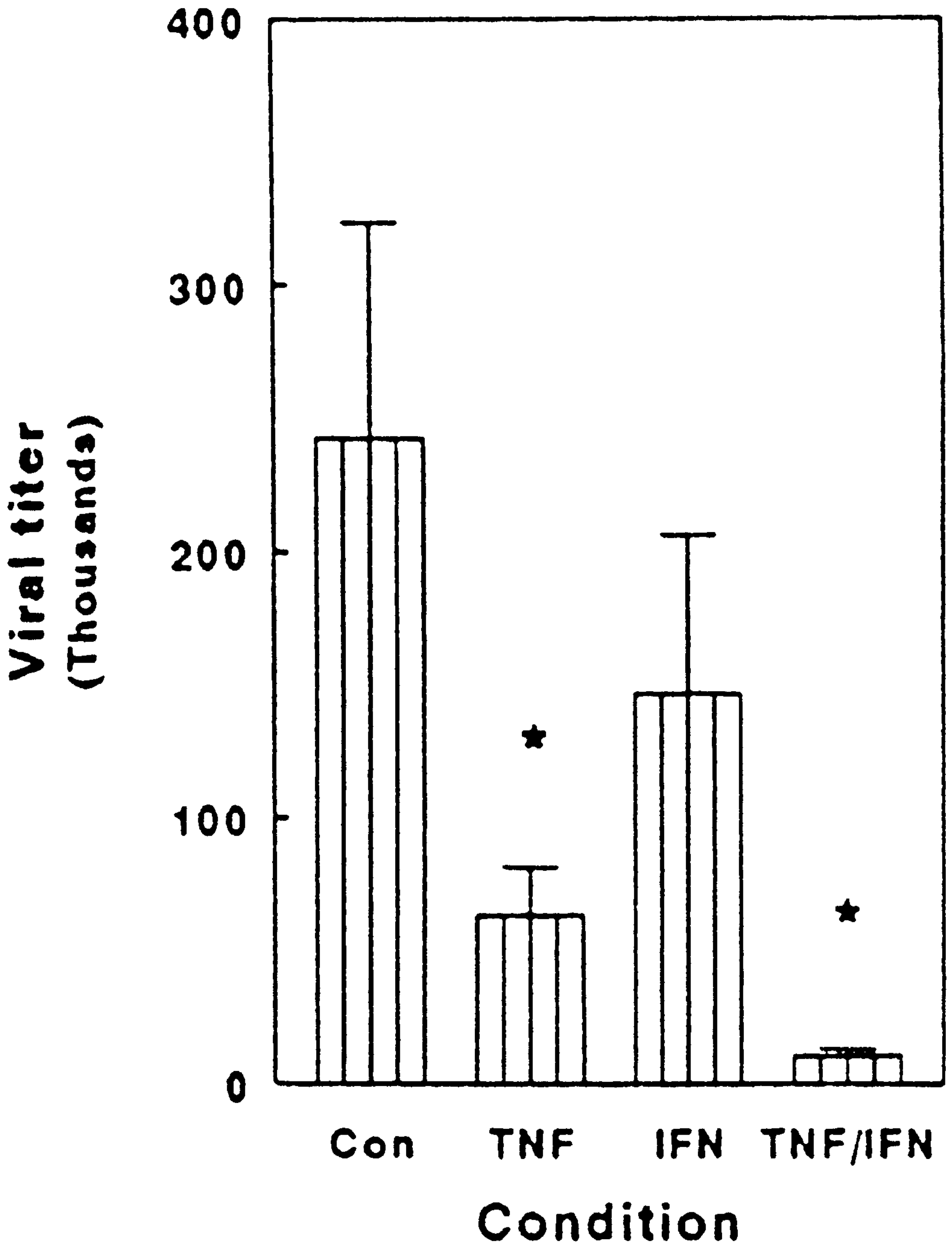

FIG. 3C indicates the effects of TNFα and IFN-β alone, and in combination, on RSV replication in A549 cells following infection with an MOI=1. Monolayers were exposed for 16 hours to TNFα (100 ng/ml), IFN-β (2 LU/ml), or both (same concentrations) and total RSV production was determined. Results shown are mean+SEM. *P<0.05 comparing TNFα or TNFα/IFN-β to controls.

Figure 4A:
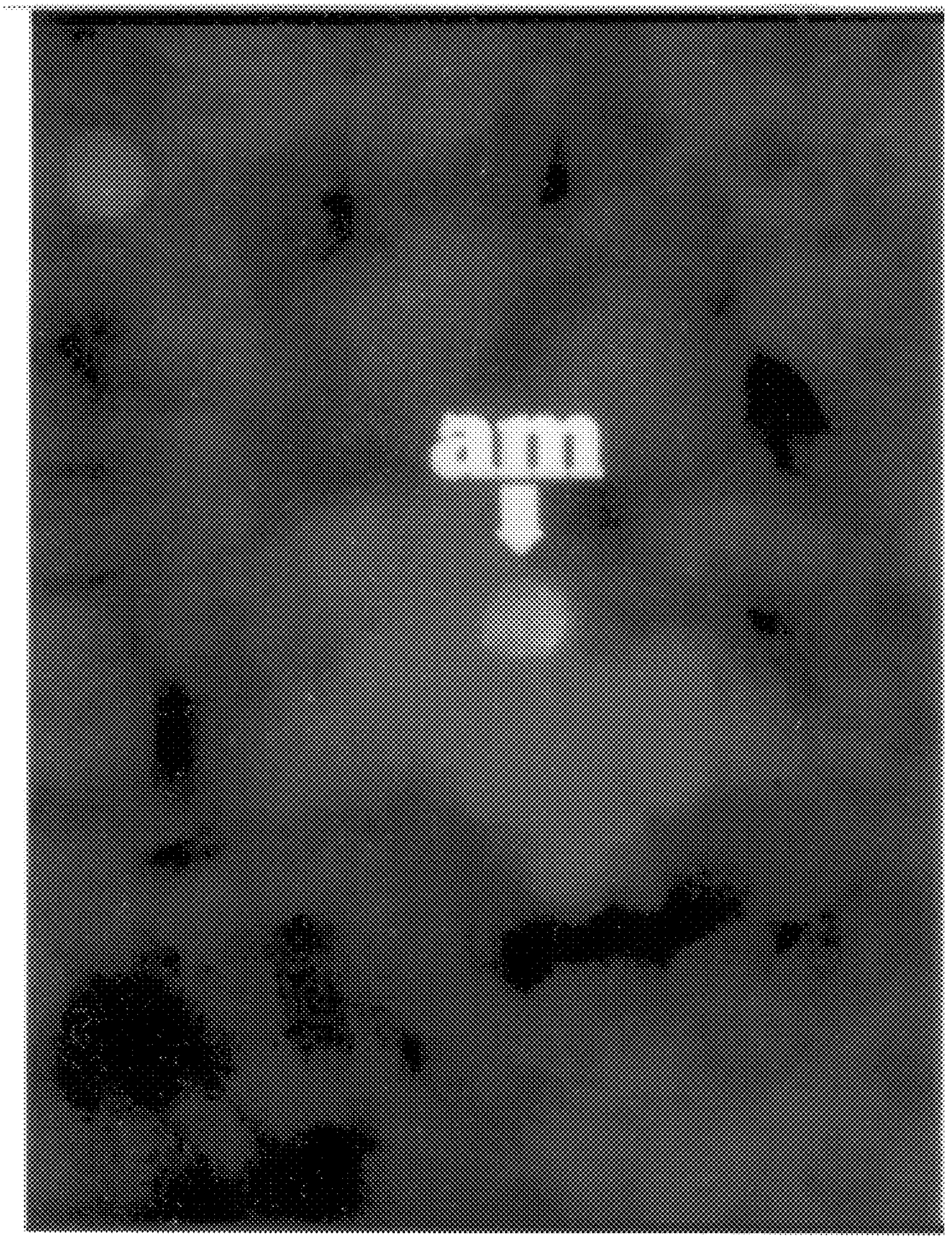
Figure 4B:
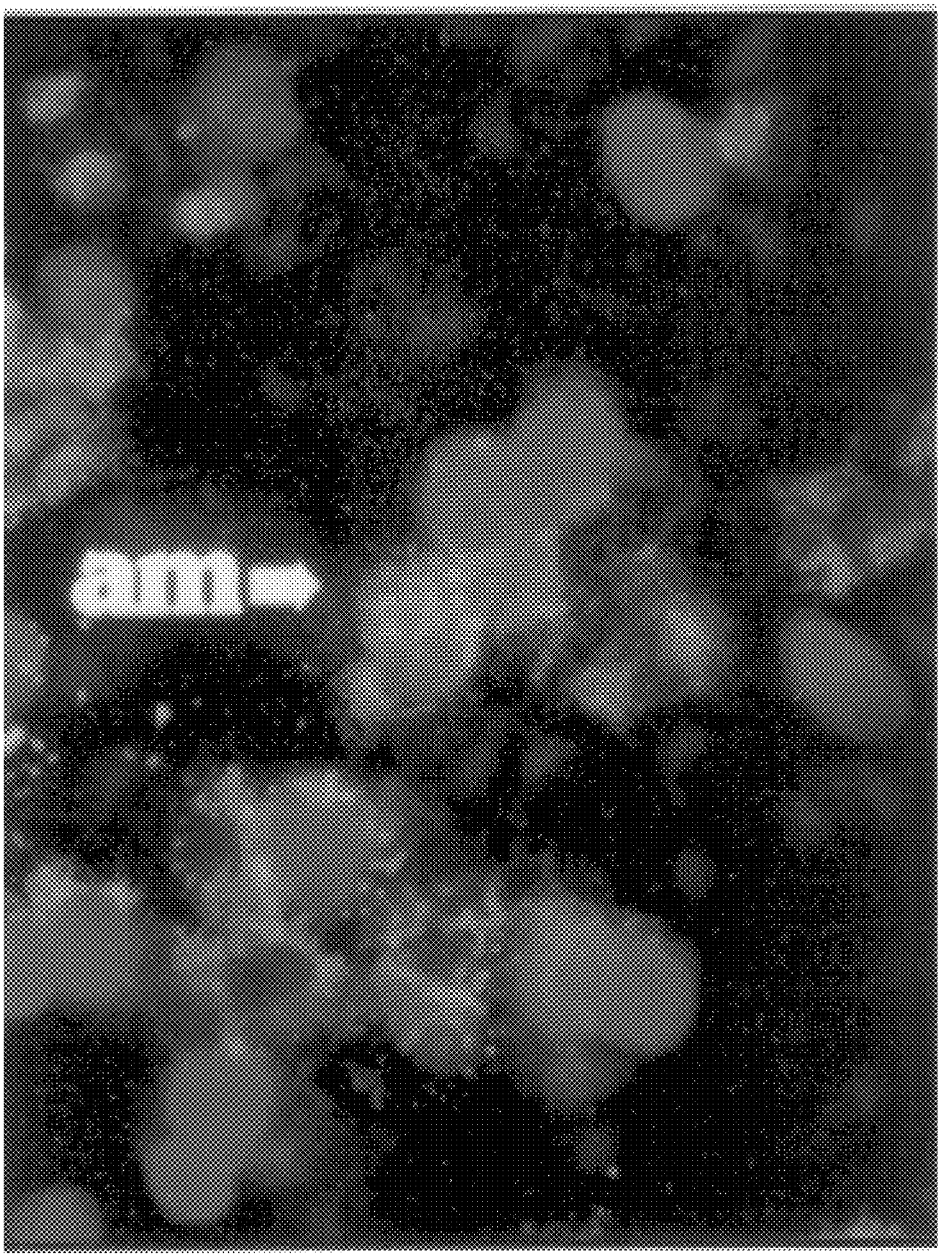
Figure 4C:
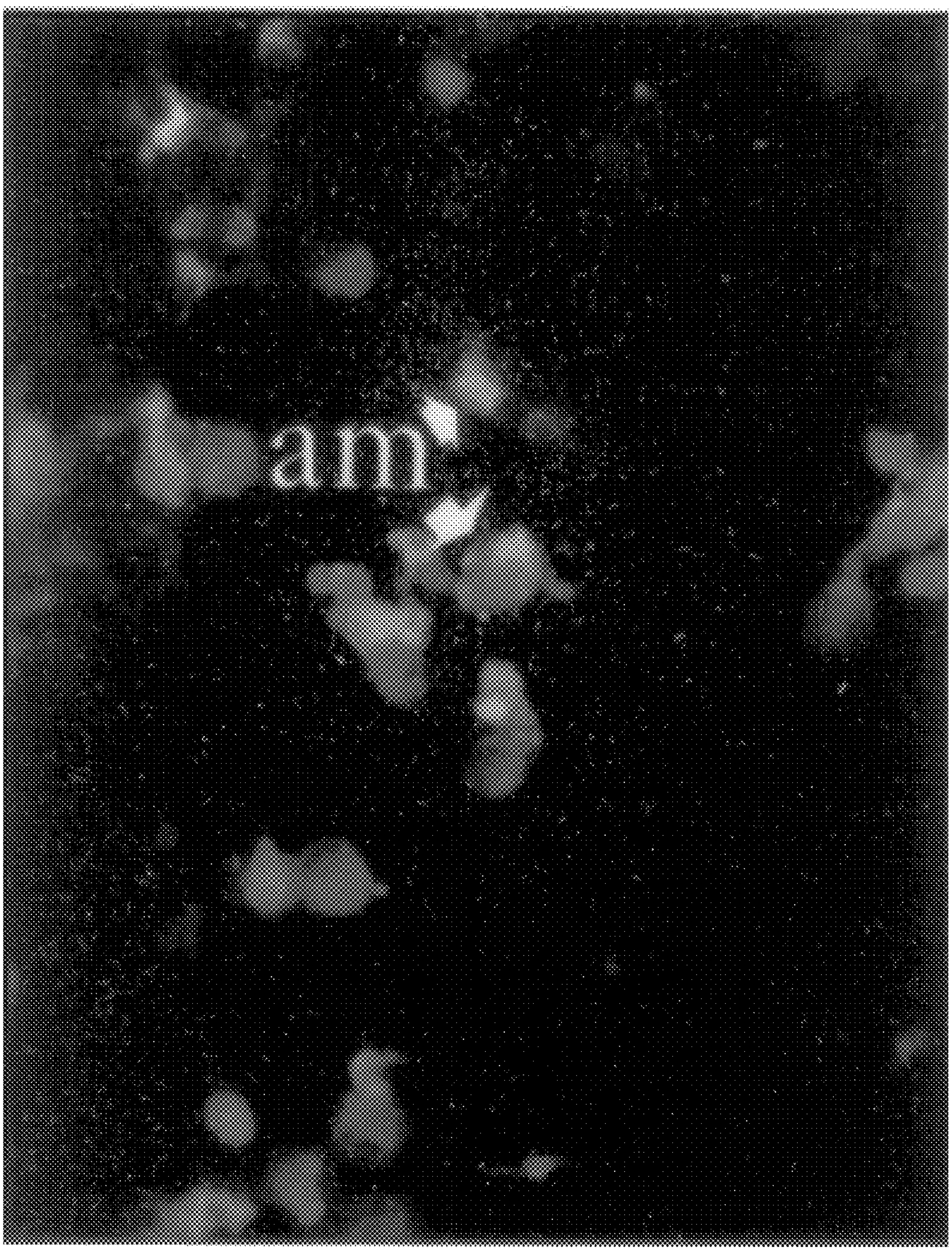
Figure 4D:
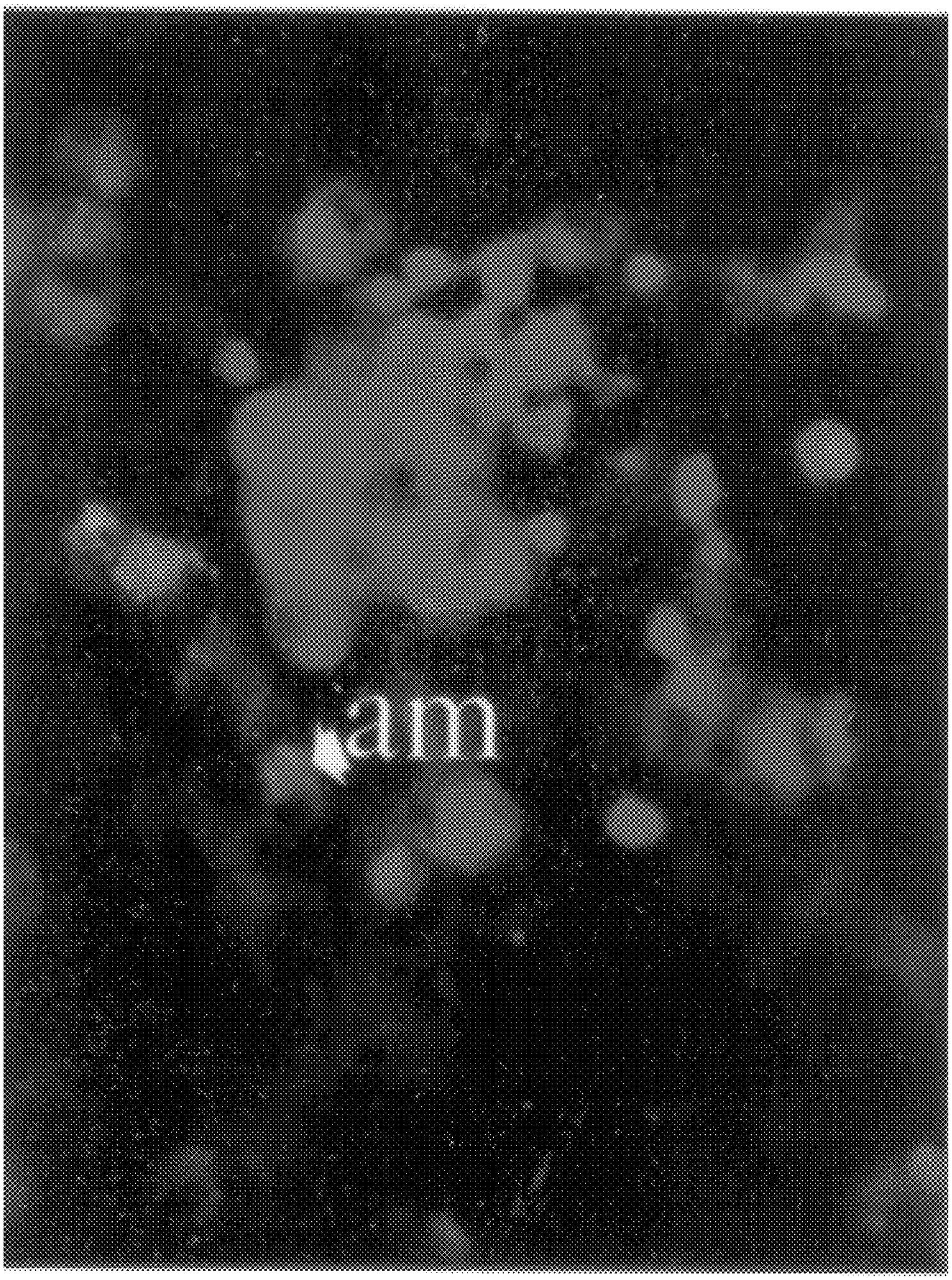

FIGS. 4A–4D are photomicrographs showing the transmission of RSV between alveolar macrophages, 9HTE, and CV-1 cells determined by direct immunofluorescent microscopy as described in the Examples. FIG. 4A, RSV infected alveolar macrophages at 24 h p.i. were added to uninfected monolayers of 9HTE cells. FIG. 4B, RSV infected 9HTE cells were added to uninfected alveolar macrophages. FIG. 4C, RSV infected alveolar macrophages were added to uninfected CV-1 cells. FIG. 4D, RSV infected CV-1 cells were added to uninfected alveolar macrophages. Alveolar macrophages (am) were identified by morphology and are indicated by arrows. Co-cultures were fixed and stained for RSV protein expression (yellow-green fluorescence) and Evans blue (red) counterstain. Panels A and B, magnification×400; FIGS. 4C and 4D, magnification×200.

DETAILED DESCRIPTION OF THE INVENTION

The above and various other objects and advantages of the present invention are produced by inhibiting respiratory syncytial virus (RSV) and other respiratory RNA viruses through the administration of exogenous, recombinant or natural interferon-beta (IFN-β). Preferably, the exogenous IFN-β is administered to the respiratory tract of a host susceptible or suffering from infection by RSV and potentially other RNA respiratory viruses by inhalation including the use of effective nebulized or aerosol doses of IFN-β. Application of exogenous IFN-β via nebulization, coupled with endogenous tumor necrosis factor (TNFα) production by the airway luminal cells in RSV infected patients, interact to restrict RSV replication. This results in an improved therapeutic treatment against respiratory virus infections.

In this regard, acute RSV induced lung disease and chronic lung abnormalities are believed to result from replication of virus in airway epithelial cells yielding syncytia and denudation of the epithelium, as well as collateral injury of uninfected cells secondary to the inflammatory response. These postulates have not been rigorously examined in human lung epithelial cells nor is it known if these cells possess intrinsic mechanisms to restrict RSV.

As a result, applicants have employed three human lung epithelial cell lines as models (see examples below) to demonstrate that these cells: (i) are permissive to RSV infection and support virus replication in a dose/time dependent manner; (ii) respond to TNFα to restrict RSV replication through an apparent receptor mediated process; (iii) respond to IFN-β alone, or in combination with TNFα, to essentially abort RSV replication; (iv) respond to pretreatment as well as simultaneous treatment with TNFα and IFN-β to markedly restrict RSV and; (v) transmit RSV to uninfected alveolar macrophages yet resist transmission of virus from RSV infected alveolar macrophages. These results indicate that the expression of endogenous TNFα or use of exogenous IFN-β have an important role in restricting RSV replication in human lung epithelial cells.

More particularly, the present invention is directed to the use of combining exogenous, nebulized INF-β to the airways coupled with endogenous TNFα, produced by resident alveolar macrophages, to generate therapeutic benefits in RSV infected individuals. Since RSV replicates exclusively in luminal respiratory cells, the targets for anti-viral therapy are organ directed and are narrowly defined. Moreover, since the volume of epithelial lining fluid (that fluid bathing the luminal airway cells) is approximately 10 ml in a one (1) year old and 30 ml in a five (5) year old, the amount of nebulized IFN-β necessary to achieve an anti-viral dose is substantially less than that which would be required if the drug were administered systemically.

Along these lines, it is noted that while systemic (as opposed to nebulized) administration of IFN-α (and not IFN-β) has been used safely to treat RSV resulting in some clinical improvement (Sung RYT et al., *Arch. Dis. Child*, 69:440–442, 1993), no demonstrable change in virus shedding has been observed. Further, it is noted that this study did not determine whether effective levels of IFN were achieved at luminal airway cells. Consequently, these results differ substantially from the present invention.

Specifically, as more particularly discussed in the examples below, applicants have determined that IFN-β interacts with appropriate receptors on airway epithelial cells to restrict RSV replication. Since evaluation of the studies set forth in the Examples, applicants have determined that IFN-β inhibits RSV replication in the 9HTE (tracheal) and BEAS 2B(bronchiolar) human cell lines. In addition, applicants have also shown that in six (6) separate human donors, IFN-β inhibits RSV replication in primary lung epithelial cell explants (unpublished results).

These results indicate that human lung epithelial cells express receptors which facilitate organ-specific targeted delivery of IFN-β and minimize systemic effects. Furthermore, IFN-β may not induce the profound immunologic alterations associated with IFNγ that might adversely alter the immune response to RSV.

As a result, the present invention represents a new and effective way of treating viral infections in the respiratory tract. Through the use of IFN-β in nebulized form, therapeutic effects against virus infection are produced. In the content of the present invention, a therapeutically effective amount of INF-β refers to the amount of INF-β to restrict the production of RNA viruses such as RSV in lung epithelial cells.

As used herein, "interferon-β" or "IFN-β" refers to all forms of beta interferon as are known to be active in accepted IFN-β assays, such as by inhibition of encephalomyocarditis virus replication in A549 cells, neutralization by antibodies having immunoreactivity for IFN-β but not IFN-α or IFN-gamma, heat lability, etc . . . Moreover, TNFα, as employed herein, refers, in general, to the various forms of TNF-alpha which exhibit one or more biologic properties of tumor necrosis such as tumor cell lysis, inhibition of infectious agents, and are neutralized by antibodies to TNF-alpha (α) but not antibodies to TNF-beta (lymphotoxin) or other cytokines.

In addition, the IFN-β utilized in this invention is that of recombinant or natural type. Specifically, IFN-β produced in recombinant cell culture, from natural isolates or by stable untransformed cell lines are satisfactory for use herein. Suitable IFN-β, includes those available from Toray Pharmaceuticals, Hoffman La Roche and others. Optionally, TNFα may also be included in the method and composition of the present invention. The TNFα utilized includes the products of recombinant or untransformed cell culture. Suitable TNFα include those available from Genentech. In practice of the invention, the dosage of IFN-β and/or TNFα will vary as it is understood by one skilled in the art. Several variables will be taken into account in determining the appropriate properties of IFN-β or TNFα to be used, the concentration of INF-β and/or TNFα in the therapeutic compositions and the dosages to be administered. These include, the clinical conditions of the patients and others. Consequently, as it is understood by those of skill in the art, dosages and treatment regimens will typically be modified according to the attendant circumstances and medical conditions.

For the purposes of the present invention, lyophilized human IFN-β is provided at $3\times10^6$ IU/vial (calibrated by NIH international standard) by Toray Industries, Inc. of Tokyo, Japan. In addition to the purified human INF-β protein, the lyophilized preparation control contains 9 mg/vial of human serum albumin and 1 mg/vial of D-lactose. For utilization, the lyophilized human INF-β preparation is dissolved in a pharmaceutically accepted vehicle such as sterile distilled water and/or sterile physiological saline. In addition, one or more carriers, stabilizers, surfactants, buffers, anti-inflammatory agents, antibiotics, etc., may be included in the IFN-β preparation in order to enhance the effectiveness of the IFN-β active agent. The IFN-β preparations are provided as sterile aqueous solutions.

Preferably, the IFN-β is administered by inhalation over several minutes with use of a nebulizer or the like. As briefly indicated, dosage and frequency of inhalation may vary, depending on the patient's symptoms or conditions.

A wide variety of nebulizers can be utilized to deliver the composition of the present invention to the lung epithelial cells. As defined herein, a nebulizer includes all means of delivering the IFN-β compositions of the present invention in a fine spray or mist From liquid. The size of the particle produced will depend upon the method of nebulization utilized. The fine spray or mist may be produced by passing air through a liquid or by vibrating a liquid at a high frequency so that the particles produced are extremely small. In addition, the composition can be propelled by a pressure differential created by the release of a pressurized propellant or by a stream of air drawn through or created by a mechanical device.

The method and composition of this invention are useful in preventing or treating active infections of RNA viruses such as RSV. Other specific viruses include the paramyxoviruses such as parainfluenza viruses I, II, III, IV, mumps, and avian parainfluenza virus type 1-6.

Further, the method and composition of the present invention is useful in treating RNA virus infection, such as RSV, in mammals, including man, bovine, and primates. Since these viruses are conveniently transmitted through the respiratory tract, use of the nebulized or aerosolized compositions of the present invention is deemed to be an effective route of administration. This is particularly true since INF-β can be administered as a nebulized pharmaceutical agent without toxicity.

EXAMPLES

The following examples serve to illustrate the present invention and are not intended to limit the scope of this invention

MATERIALS AND METHODS

Cell lines

A549, CV-1, and U937 cell lines were obtained from the American Tissue Culture Collection (ATCC CRL #185, 70, 1593, respectively) and were propagated in DMEM (JRH Biosciences, Lenexa, Kans.), EMEM (Sigma, St. Louis, Mo.), or RPMI 1640 (Gibco BRL, Life Technologies, Grand Island, N.Y.), respectively, supplemented with 10% (v/v) fetal bovine serum (Hyclone, Logan UT), 1 mM non-essential amino acids, 1 mM sodium pyruvate, 2 mM L-glutamine, 100 μg/ml penicillin, 100 μg/ml streptomycin and 0.25 μg/ml amphotericin B (all from Sigma, St. Louis, Mo.) (DMEM, EMEM or RPMI culture media). 9HTE cells were kindly provided by Dr. D. C. Gruenert (Cardiovascular and Cancer Research Institute, University of California, San Francisco Calif.) and were propagated in MEM culture media as described (Gruenert, D. C., Basbaum, C. B., Welsh, M. J., Li, M., Finkbeiner. W. E., and J. A. Nadel. 1988. Characterization of human tracheal epithelial cells transformed by an origin defective simian virus 40 *Proc. Natl. Acad. Sci.* 85:5951–5955). BEAS 2B cells were kindly provided by Dr. C. C. Harris (Laboratory of Human Carcinogenesis, National Cancer Institute, Bethesda, Md.) and were propagated in LHC-8 media (BioFluids, Rockville Md.) supplemented with 100 μg/ml penicillin, 100 μg/ml streptomycin and 0.25 μg/ml amphotericin B as described (Reddel, R. R., Ke, Y., Gerwin, B. 1., McMenamin, M. G., Lechner, J. F., Su, R. T., Brash, D. E., Park, J. B., Rhim, J. S., and C. C. Harris. 1988. Transformation of human bronchial epithelial cells by infection with SV40 or adenovirus-12 SV40 hybrid virus, or transfection via strontium phosphate coprecipitation with a plasmid containing SV40 early region genes. *Can. Res.* 48:1904–1909). All cell lines were passaged twice a week.

Preparation of alveolar macrophaces

Fourteen normal, non-smoking donors without respiratory disease or symptoms of viral infection within the preceding four weeks underwent bronchoscopy and bronchoalveolar lavage exactly as applicants have described previously (Panuska, J. R., Midulla, F., Cirino, N. M., Villani, A., Gilbert, I. A., McFadden, E. R., and Y. T. Huang. 1990. Virus-induced alterations in macrophage production of tumor necrosis factor and prostaglandin $E_2$. *Am. J. Physiol* (*Lung Cell Mol Physiol*) 259:L396–L402; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–119). All studies were approved by the institutional review board of University Hospitals of Case Western Reserve University and informed written consent was obtained from all donors. Alveolar macrophages were purified by adherence to plastic tissue culture dishes as previously described (Panuska, J. R., Midulla, F., Cirino, N. M., Villani, A., Gilbert, I. A., McFadden, E. R., and Y. T. Huang. 1990. Virus-induced alterations in macrophage production of tumor necrosis factor and prostaglandin $E_2$. *Am. J. Physiol* (*Lung Cell Mol Physiol*) 259:L396–L402; Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–119) for 1 hour at 37° C. in 5% $CO_2$ in RPMI 1640 containing 10% (v/v) fetal bovine serum and the antibiotic supplements listed above.

RSV propagation, infection and replication

RSV stocks were prepared in CV-1 cells as previously described (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–1193) and stored at −70° C. until used. Cell lines were infected with RSV at the multiplicity of infection (MOI) listed in the text while alveolar macrophages were infected at an MOI of 3 pfu/cell. Adherent cell monolayers were exposed to virus at 37° C. in 5% $CO_2$ for 2 hours then virus inocula were removed by two washes with culture media. Cultures were incubated for the times listed in the text at 37° C. in 5% $CO_2$.

Percentage of RSV infected cells were determined by direct immunofluorescent staining with monoclonal antibodies (Mab) directed against RSV surface glycoproteins (gift of Bartels Immunodiagnostics, Bellevue, Wash.) using methods previously described (Panuska, J. R., Hertz, M. l., Taraf, H., Villani, A., and N. M. Cirino. 1992. Respiratory syncytial virus infection of alveolar macrophages in adult transplant patients. *Am. Rev. Respir. Dis.* 145:934939; [Midulla, F., Villani, A., Panuska, J. R., Dab, l., Kolls, J. K., and R. Merolla. 1993. Respiratory syncytial virus lung infection in infants: Immunoregulatory role of infected alveolar macrophages. *J. Infect Dis.* 168:1515–1519.] Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–119).

Briefly, epithelial cells were plated on eight well LabTech™ slides (Nunc Inc., Naperville, Ill.) at the doses and times described in the text, then fixed with 4% (wt/vol) paraformaldehyde in a buffer containing 25 mM HEPES, 60 mM PIPES, pH 6.9, 5 mM $MgCl_2$ and 1.5 mM GTP. After 30 min, slides were treated with 0.1% Triton X100 in 10 mM phosphate, pH 7.4, 150 mM NaCl (PBS) for 90 seconds then washed four times in PBS containing 1 mg/ml bovine serum albumin (PBS/BSA). Slides were then reacted for 1 hour at room temperature with anti-RSV Mab coupled to fluorescein isothiocyanate. Slides then were washed 3 times with PBS/BSA and overlaid with PBS 10% (v/v) glycerol. Slides were viewed with a Nikon Diaphot microscope under bright light and epifluorescent microscopy to enumerate total and fluorescent positive cells, respectively. The percentage of fluorescent positive/total cells were determined on at least 300 cells per condition.

Virus replication was determined in aliquots of sonicated cells cultures by adding serial two-fold dilutions in triplicate to monolayers of CV-1 cells grown on 96 well tissue culture plates exactly as described previously (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–119)). Viral titer is expressed as plaque forming units/$10^6$ cells to correct for differences in cell size/number at equivalent levels of monolayer confluences.

Cytokine Effects on RSV Replication

A549, BEAS 2B, 9HTE and CV-1 cell lines were treated with trypsin (Sigma, St. Louis, Mo.), counted by trypan blue exclusion, and plated at a concentration of either $3.5\times10^5$ cells/ml (A549, 9HTE, CV-1), or $5.0\times10^5$ cells/ml. (BEAS 2B, because of their smaller size and lower protein content per cell). A549, BEAS 2B, 9HTE and CV-1 cell monolayers were incubated for the times indicated in the text at 37° C. in 5% $CO_2$ with recombinant TNFα (a gift of Genentech, San Francisco Calif.) and/or human IFN-β (a kind gift of Dr. Jun Utsumi, Toray Industries Inc. Tokyo, Japan) at the doses listed in the text. Cells were then infected for 2 hours with RSV at an MOI of 1, washed twice in fresh culture media, and incubated for 48 hours. The epithelial monolayers were harvested by scraping and ice-cold aliquots were sonicated twice at maximal output in an Artek Sonic Dismembrator prior to titration for infectious virus as described above.

TNFα Receptor Assays $[^{125}I]$-TNFα (specific activity 42 μCi/μg) was purchased from Amersham Corp. (Arlington Heights, Ill.). A549, 9HTE, BEAS 2B, and CV-1 were grown as monolayers in tissue culture plates and washed twice PBS/BSA. U937 cells were treated with phorbol myristeric acetate for 24 h as described previously (Villani, A., Cirino, N. M., Baldi, E., Kester, M., McFadden, E. R., J. R. Panuska. 1991. Respiratory syncytial virus infection of human mononuclear phagocytes stimulates synthesis of platelet-activating factor. *J. Biol Chem.* 266:5472–5479), washed twice with PBS/BSA, then used in assays. $[^{125}I]$-TNFα was added to duplicate wells and incubated at 4° C. for 1 hour. Duplicate wells containing 100 fold molar excess of recombinant TNFα were analyzed in parallel. Unbound radioactivity was aspirated and cell monolayers were washed twice in ice-cold PBS/BSA. Monolayers were lysed with 0.5% (w/v) NP-40 and counted in a Micromedic Apex® gamma counter. Parallel wells containing monolayers of each cell type were lysed with distilled water and protein concentration determined utilizing a dye protein assay (Bio-Rad Laboratories, Melville, N.Y.). Specific binding was expressed as counts per minute per mg of cellular protein.

Cellular expression of the 55 and 75 kDa TNFα receptors were determined by enzyme linked immunoabsorbent assays using minor modifications of previously described methods (Higuchi, M., and B. B. Aggarwal. 1992. Microtiter plate radioreceptor assay for tumor necrosis factor and its receptors in large numbers of samples. *Analytical Biochem.* 204:53–58). Briefly, lung epithelial, CV-1, or U937 cells were washed×3 in PBS, two fold serially diluted in PBS, then fixed in 100% ice-cold methanol for 5 minutes. Fixed cells were then treated for 5 minutes in 6% $H_2O_2$ in 94% methanol. Fixed cells were washed×2 in PBS/BSA and incubated in the absence or presence of Mab to the 55 and/or 75 kDa TNFα receptor (Genzyme, Cambridge, Mass.) at 20 μg/ml in PBS for 1 hour at 4° C. Cells were washed×2 with PBS/BSA then reacted with biotin labeled goat anti-mouse antibodies at 0.1 μg/ml (Kirkegaard and Perry, Gaithersburgh, Md.) and incubated on ice for 30 minutes. Cells were then washed×2 in PBS/BSA and reacted with 0.1 μg/ml streptavidin peroxidase (Kirkegaard and Perry, Gaithersburgh, Md.) and incubated on ice for 30 minutes. Cells were then washed×2 in PBS/BSA and centrifuged at 2000 rpm for 10 minutes. Cell pellets were resuspended in 250 μl $H_2O_2$ and dispensed in 50 μl aliquots to wells of a 96 well tissue culture dish. 150 μl of diaminobenzidine HCI (25 mg/ml) was added to each well and incubated for 15 minutes and absorbance at 450 nm was determined with a microtiter absorbance meter (E MAX™ Molecular Devices, Menlo Park, Calif.). Controls included samples without cells; lung epithelial cells reacted with irrelevant isotype control Mabs and the secondary antibodies; cells reacted with the secondary antibodies alone; or cells reacted in the absence or primary or secondary antibodies but exposed to diaminobenzidine HCI alone. In each case, absorbance at 450 nm was within 10% of media controls. Standard curves were generated with U937 cells shown previously to express the 55 and 75 kDa TNFα receptors (Higuchi, M., and B. B. Aggarwal. 1992. Microtiter plate radioreceptor assay for tumor necrosis factor and its receptors in large numbers of samples. *Analytical Biochem.* 204:53–58). Absorbance was determined at cell concentrations of 0, 0.2, 0.4, 1.0, 2.0 and $3.0\times10^6$ cells/ml on triplicate samples. Results were analyzed by linear regression analysis.

Cell Viability and Protein Assays

The effects of TNFα and IFN-β on cell viability were determined by trypan blue exclusion and enumeration of the percentage of cells that excluded the dye by light microscopy. Membrane damage of epithelial cells were determined by reacting monolayers with acridine orange and ethidium bromide (each at 1 μg/ml in PBS) and determining the percentage of membrane damaged cells by fluorescent microscopy as previously described (Cirino, N. M., Panuska, J. R., Villani, A., Taraf, H., Rebert, N. A., Merolla, R., Tsivitse, P., and l. A. Gilbert. 1993. Restricted replication of respiratory syncytial virus in human alveolar macrophages. *J. Gen. Virol.* 74:1527–1537; Panuska, J. R., Cirino, N. M., Midulla, F., Despot, J. E., McFadden, E. R., and Y. T. Huang. 1990. Productive infection of isolated human alveolar macrophages by respiratory syncytial virus. *J. Clin. Invest* 86:113–119). Acridine orange stains the nuclei of viable cells green while ethidium bromide stains the nuclei of nonviable cells orange. The effects of TNFα and IFN-β on cell growth were determined by extensively washing monolayers with PBS, lysing the monolayers with distilled water, and two cycles of freeze/thaw. Cellular protein concentration was then determined as described above as a function of time following treatment with these cytokines or media controls. Cellular proteins were analyzed by sodium dodecyl sulfate (SDS) electrophoresis on 10% (w/v) polyacrylamide gels with Coomassie blue staining as previously described (Panuska, J. R., Fukui, K., and C. W. Parker. 1988. Secreted proteins of human monocytes. *Biochem. J.* 249:501–511).

Transmission of RSV between Epithelial, CV-1 cells and Alveolar Macrophages.

Epithelial cells were infected with RSV at an MOI=1 then harvested at 24 hours post-infection and added to monolayers of uninfected alveolar macrophages. In parallel, alveolar macrophages were infected with RSV at an MOI=3 then harvested at 24 h post-infection and added to monolayers of uninfected epithelial cells. In some experiments, RSV infected alveolar macrophages were mixed with 500 U/ml of a neutralizing antibody to TNFα (Amersham Corp., Arlington Heights, Ill.) prior to addition to epithelial monolayers. Co-cultures were overlaid with 0.5% (w/v) agarose in culture media and incubated for 48 hours at 37° C. in 5% $CO_2$. Co-cultures were then fixed in methanol/acetone as previously described (Panuska, J. R., Hertz, M. I., Taraf, H., Villani, A., and N. M. Cirino. 1992. Respiratory syncytial virus infection of alveolar macrophages in adult transplant patients. *Am. Rev. Respir. Dis.* 145:934939; Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537) and stained for RSV protein expression by direct immunofluorescence as described above. Cell types were discriminated by morphology.

Statistical Analysis

All results shown are mean±standard deviation (SD) or standard error of the mean (SEM) as indicated in the text. The effects of dose were determined by analysis of variance (ANOVA) and comparisons between means were determined by Student's t-tests. Multiple t-test analyses were corrected by the Bonferroni method. Probability (P) values less than 0.05 were considered significant.

RESULTS

RSV replication in BEAS 2B, A549, and 9HTE epithelial cells

BEAS 2B, A549, 9HTE and CV-1 cells exposed to RSV, then extensively washed to remove virus inocula, demonstrated a significant (P<0.01, ANOVA) virus dose dependent increase in virus production at 48 h p.i., FIG. 1A. Virus production in sonicated cells and supernatants were maximal in all cell lines at 48 h p.i. (P<0.01, Student's t-tests), FIG. 1B. Accumulation of infectious RSV was decreased at 72 and 96 h p.i. probably due to lysis of epithelial cell monolayers and instability of virus at 37° C. as previously reported (Mcintosh, K. and R. M. Chanock. 1990. Respiratory syncytial virus. In B. N. Field, D. M. Knipe et al., editors. Virology, Second Edition, Raven Press, Ltd., New York, Chapter 38, 1045–1072; Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537). Virus replication per $10^6$ cells at 48 h p.i. was highest in CV-1 (~$4\times10^6$)>A549 (~$1.8\times10^6$)>9HTE (~$0.1\times10^6$)>BEAS 2B cells (~$0.1\times10^6$). All cell lines released infectious virus but viral titer in cell-free supernatants were less than 20% of total cellular virus at all time points (not shown). These results suggested that the site of origin, transformation with SV-40 (BEAS 2B and 9HTE), or the state of differentiation of these lung epithelial cells determined their capacity to replicate RSV.

Effects of TNFα and IFN-β on RSV replication in lung epithelial cells

RSV induces alveolar macrophages to produce TNFα in vivo (Midulla, F., Villani, A., Panuska, J. R., Dab, I., Kolls, J. K., and R. Merolla. 1993. Respiratory syncytial virus lung infection in infants: Immunoregulatory role of infected alveolar macrophages. *J. Infect Dis*. 168:1515–1519; Hayes, P. J., Scok, R., and J. Wheeler. 1994. In vivo production of tumor necrosis factor α and interleukin-6 in BALB/c mice inoculated intranasally with a high dose of respiratory syncytial virus. *J. Med. Virol* 42:323–329) which can function as a potent anti-viral cytokine (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol*. 74:1527–1537; Wong, G. H. W., Tartaglia, L. A., Lee, M. S., and D. V. Goeddel.1992. Antiviral activity of tumor necrosis factor (TNF) is signaled through the 55-kDa receptor, type 1 TNF. *J. Immunology* 149:3350–3353; Wong, G. H. W., Kamb, A., and D. V. Goeddel.1993. Antiviral properties of TNF. In B. Beutler, editor. Tumor Necrosis Factors: The Molecules and Their Emerging Role in Medicine. Raven Press. Ltd, New York, 371–381). Pretreatment of lung and CV-1 cells with recombinant TNFα (rTNFα) yielded a significant (P<0.05, ANOVA) dose dependent inhibition of RSV replication in BEAS 2B, A549, and 9HTE cells, but not CV-1 cells, compared to media controls, FIG. 2. CV-1 cells pretreated with rTNFα at doses as high as 5000 μg/ml replicated RSV as efficiently as untreated cells, consistent with prior work (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol*. 74:1527–1537).

TNFα and IFN-β can interact to restrict replication of some viruses. Pretreatment of lung cells with IFN-β (100 IU/ml) for 16 hours markedly restricted RSV replication, Table 1.

TABLE 1

Effects of IFN-β (100 IU/ml) on lung epithelial and CV-1 cell replication of RSV.

| CELL TYPE | % INHIBITION OF RSV REPLICATION* |
|---|---|
| CV-1 | 83.2 ± 12.2 |
| BEAS 2B | 92.2 ± 4.5 |
| 9HTE | 77.8 ± 13.1 |
| A549 | 96.6 ± 8.6 |

*Results shown are mean ± SD of triplicate samples each two-fold serially diluted to provide replicates of six. Results are from a single experiment, performed in parallel, representative of two separate experiments.

In contrast to TNFα, IFN-β potently inhibited RSV replication in CV-1 cells indicating these cytokines can activate separate anti-viral pathways. The effects of IFN-β dose were examined with A549 lung epithelial cells. Pretreatment with IFN-β for 16 h prior to infection with RSV (MOI=1) demonstrated a dose dependent inhibition of RSV replication in A549 cells yielding essentially complete inhibition of RSV replication at doses>20 IU/ml, FIG. 3A. IFN-β doses of 20 IU/ml were as potent in inhibiting RSV replication as was TNFα (compare with FIG. 2). To investigate if pretreatment with TNFα and/or IFN-β was necessary to inhibit RSV replication, A549 cells were pretreated with these cytokines for 16 hours, simultaneously treated at the time of RSV exposure, or treated at 4 h p.i. Simultaneous treatment decreased RSV replication to a similar extent as pretreated cells, however addition of TNFα or IFN-β at 4 h p.i. was significantly (P<0.05) less effective, FIG. 3B. To determine if TNFα and IFN-β interacted to inhibit RSV, A549 cells were pretreated with submaximal inhibitory doses of TNFα (100 μg/ml) and IFN-β (2 IU/ml) separately, and in combination. As shown in FIG. 3C. TNFα and IFN-β interacted to inhibit RSV replication. This interaction appeared additive, and not synergistic, when analyzed by isobolographic analysis (not shown).

TNFα Receptor Expression

The TNFα mediated dose (FIG. 2) and time (FIG. 3) dependent inhibition of RSV replication in lung epithelial, but not CV-1 cells, suggested that these cells might differentially express TNFα receptors that could transduce the signal resulting in restricted viral replication. [$^{125}$I]-TNFα binding studies of adherent cell monolayers and U937 cells, as a positive control (Higuchi, M., and B. B. Aggarwal. 1992. Microtiter plate radioreceptor assay for tumor necrosis factor and its receptors in large numbers of samples. *Analytical Biochem*. 204:53–58), were performed in the absence or presence of a 100 fold excess of rTNFα. Results indicated that all cell types specifically bound TNFα although less binding was observed with CV-1 cells per mg cellular protein than were seen with BEAS 2B and 9HTE cells, Table 2.

TABLE 2

TNFα receptors on lung epithelial and CV-1 cells

| Cell Type | [$^{125}$I]TNF bound (cpm/mg cellular protein) | 55 kDa receptor (absorbance/ $10^6$ cells) | 75 kDa receptor (absorbance/ $10^6$ cells) |
|---|---|---|---|
| CV-1 | 3,072 ± 1,055 | 0.17 ± 0.02 | 0.13 ± 0.01 |
| BEAS 2B | 54,596 ± 7,892* | 0.35 ± 0.05* | 0.17 ± 0.05 |
| 9HTE | 11,461 ± 4,991* | 0.25 ± 0.02 | 0.13 ± 0.06 |
| A549 | 4,721 ± 1,756 | 0.57 ± 0.14* | 0.22 ± 0.08 |
| U937 | 15,494 ± 1,523* | 0.26 ± 0.02 | 0.33 ± 0.02* |

Results shown are mean ± SD, n = 3 for [$^{125}$I]TNFα binding.
TNFα receptor expression for the 55 and 75 kDa subtypes was determined by ELISA and results shown were determined by linear regression analysis of absorbance versus cell number as described in Methods.
*P, 0.05 compared to CV-1 cells (Student's t-tests).

Consistent with these results, all cell types expressed detectable proteins for the 55 and 75 kDa TNFα receptors assessed by ELISA with Mabs to these receptor subtypes, Table 2. U937 cells express both the 55 and 75 kDa TNFα receptors (Higuchi, M., and B. B. Aggarwal. 1992. Microtiter plate radioreceptor assay for tumor necrosis factor and its receptors in large numbers of samples. *Analytical Biochem*. 204:53–58) and were used as a positive control. Omission of either the primary Mabs or secondary antibodies yielded absorbance values that did not differ by greater than 10% from media controls. Although TNFα binding and protein expression did not show strict concordance, this could result from differences in receptor affinity, steric availability on cell membranes, or receptor turnover. Nevertheless, expression of the 55 and 75 kDa TNFα receptors did not appear to account for the differential effects of TNFα on RSV replication in lung epithelial versus CV-1 cells.

Effects of TNFα on RSV Infection, Cell Growth, and Viability of Epithelial Cells TNFα can restrict virus replication by interfering with infection, inhibiting cell growth, lysis of virus infected cells, or induction of other anti-viral pathways (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537; Wong, G. H. W., Tartaglia, L. A., Lee, M. S., and D. V. Goeddel.1992. Antiviral activity of tumor necrosis factor (TNF) is signaled through the 55-kDa receptor, type 1 TNF. *J. Immunology* 149:3350–3353; Wong, G. H. W., Kamb, A., and D. V. Goeddel.1993. Antiviral properties of TNF. In B. Beutler, editor. Tumor Necrosis Factors: The Molecules and Their Emerging Role in Medicine. Raven Press. Ltd, New York, 371–381). These possible mechanisms were examined sequentially by applicants.

All lung epithelial cells, when pretreated with rTNFα (1000 ng/ml) prior to RSV infection (MOI=0.1), demonstrated a small 30±8%, but significant (n=4, P<0.05), reduction in infected cells at 48 h p.i. determined by direct immunofluorescence compared to untreated cells. This was not observed with lung cells infected with a 10 fold higher RSV dose (MOI=1) (93+4 vs. 96+6% infected cells in rTNFα pretreated vs. media controls, respectively, n=4, P=NS). Thus, sufficient RSV dose overcame the anti-infective effects of TNFα and suggested that TNFα could also interfere with virus replication at a step distal to initial infection.

TNFα did not significantly reduce cell growth or viability of BEAS 2B, A549 and 9HTE cells. All lung epithelial cells pretreated for 16 h with rTNFα (1000 ng/ml) demonstrated a 3.1±0.8 fold increase in cellular protein concentration and a 2.9±0.9 fold increase in viable cell number at 48 h post-treatment which differed by less than 20% compared to epithelial cells treated with culture media alone (n=3, P=NS). Cell membrane integrity (acridine orange/ethidium bromide staining) or viability (trypan blue exclusion) in TNFα pretreated lung epithelial cells that were mock or RSV infected were indistinguishable from media controls assessed at 24 h p.i. Under all conditions, with each epithelial cell type, the percentage of cells with intact membranes and viable was greater than 86% (n=2).

Finally, mock or RSV infected A549 and 9HTE cells pretreated for 16 hours with IFN-β, TNFα, or both, demonstrated essentially equivalent expression of cellular proteins compared to uninfected controls when lysates from equal cell numbers were analyzed by SDS polyacrylamide electrophoresis (not shown).

Transmission of RSV between epithelial cells and human alveolar macrophapes.

TNFα restricts RSV replication in alveolar macrophages and inhibits RSV infection of lung epithelial cells at low MOI (see above). To examine if TNFα, endogenously expressed by RSV infected alveolar macrophages, effected RSV transmission between these cells and lung epithelial cells, co-culture experiments were performed. Transmission of RSV from infected cells (24 hours p.i.) to uninfected cells were determined after 24 hours of co-culture under 0.5% agarose to prevent fluid phase spread of virus. RSV infection was assessed by direct immunofluorescence and cell types were discriminated by morphology. Infected 9HTE cells transmitted RSV to uninfected alveolar macrophages (FIG. 4) In contrast, RSV infected alveolar macrophages clearly adhered to epithelial monolayers but did not transmit virus to 9HTE cells, (FIG. 4B), A549 or BEAS 2B cells (not shown). Although alveolar macrophages did not transmit RSV to these lung epithelial cells, they were competent to transmit virus to the RSV permissive CV-1 cell line (FIG. 4C). RSV infected CV-1 cells transmitted RSV to uninfected alveolar macrophages similar to lung epithelial cells (FIG. 4D). These results are consistent with results applicants have previously described (Cirino, N. M., Panuska, J. R., Villani, A., Taraf, H., Rebert, N. A., Merolla, R., Tsivitse, P., and l. A. Gilbert. 1993. Restricted replication of respiratory syncytial virus in human alveolar macrophages. *J. Gen. Virol.* 74:1527–1537).

In fourteen separate donors, RSV was transmitted solely from epithelial cells to uninfected alveolar macrophages and not from RSV infected alveolar macrophages to uninfected epithelial cell lines. Transmission of RSV from infected alveolar macrophages to 9HTE cells was not altered by addition of anti-TNFα or anti-IFN-β (1000 neutralizing units/ml) to co-cultures. However, applicants interpret these results cautiously because it is possible that these cytokines interact with their receptors through sequestered spaces or prior to capture by the neutralizing antibodies.

DISCUSSION

As indicated above, acute RSV induced lung disease and chronic lung abnormalities are thought to result from replication of the virus in airway epithelial cells yielding syncytia and denudation of the epithelium, as well as collateral injury of uninfected cells secondary to the inflammatory response. These postulates have not been rigorously examined in vitro in human lung epithelial cells nor is it known if these cells possess intrinsic mechanisms to restrict RSV.

As a result, applicants here employ three human lung epithelial cells as models to demonstrate that these cells: (i) were permissive to RSV infection and supported virus replication in a dose/time dependent manner; (ii) responded to TNFα to restrict RSV replication through an apparent receptor mediated process; (iii) responded to IFN-β alone, or in combination with TNFα, to essentially abort RSV replication; (iv) responded to pretreatment as well as simultaneous treatment with TNFα and IFN-β to markedly restrict RSV and; (v) transmitted RSV to uninfected alveolar macrophages yet resisted transmission of virus from RSV infected alveolar macrophages. Thus, it has been found that expression of endogenous TNFα or use of exogenous IFN-β have a role in restricting RSV replication in human lung epithelial cells.

Lung epithelial cells supported RSV replication less efficiently than CV-1 cells. Applicants have recently discovered that lung epithelial cell lines, and primary lung epithelial cells, express constitively the enzyme 2', 5' oligoadenylate (2', 5'A) synthetase dependent RNase L which degrades viral m RNA transcripts and restricts viral replication. The 2', 5'A dependent RNase L is induced by IFN-β and may serve as the critical molecular pathway to restrict RSV replication in lung epithelium. (Panuska, J. R., Rebert, N. A., Hoffmann, S. I. Anti-Respiratory Syncytial Virus Pathways in Cytokine Treated Human Lung Cells. *Am. J. of Resp. and Crit. Care Medicine* 151:A122). These results suggest that the differentiated phenotype of lung epithelial cells may regulate their capacity to replicate RSV. A549 cells, of alveolar origin, efficiently replicated RSV and may provide a cellular model for RSV induced pneumonia which primarily effects alveolar cells. 9HTE and BEAS 2B cells derived from tracheal and bronchiolar origin, also replicated RSV, albeit less efficiently than A549 cells, but again may provide a cellular model for RSV induced conducting airway and bronchiolar inflammation. The results presented here do not permit applicants to determine if differentiated phenotype, transformation with SV-40, anatomical origin, or species derivation (human lung vs. monkey kidney cell) serve as the primary determinants controlling the efficiency of RSV replication (Gruenert, D. C., Basbaum, C. B., Welsh, M. J., Li, M., Finkbeiner. W. E., and J. A. Nadel. 1988. Characterization of human tracheal epithelial cells transformed by an origin defective simian virus 40 *Proc. Natl. Acad. Sci.* 85:5951–5955; Reddel, R. R., Ke, Y., Gerwin, B. 1., McMenamin, M. G., Lechner, J. F., Su, R. T., Brash, D. E., Park, J. B., Rhim, J. S., and C. C. Harris. 1988. Transformation of human bronchial epithelial cells by infection with SV40 or adenovirus-12 SV40 hybrid virus, or transfection via strontium phosphate coprecipitation with a plasmid containing SV40 early region genes. *Can. Res.* 48:1904–1909; Standiford, T. J., Kunkel, S. L., Basha, M. A., Chensue, S. W., Lynch, J. P., Toews, G. B., Westwick, J., and R. M. Strieter. 1990. Interleukin-8 gene expression by a pulmonary epithelial cell line. *J. Clin. Invest* 86:1945–1953). Further studies could address these possibilities.

The state of differentiation did appear to differ between lung epithelial and CV-1 cells. Lung epithelial cells treated with rTNFα markedly restricted RSV replication whereas CV1 cells were unresponsive. This did not simply reflect a lack of expression of the 55 or 75 kDa TNFα receptors which may transduce the anti-viral signal(s) (Wong, G. H. W., Tartaglia, L. A., Lee, M. S., and D. V. Goeddel.1992. Antiviral activity of tumor necrosis factor (TNF) is signaled through the 55-kDa receptor, type 1 TNF. *J. Immunology* 149:3350–3353; Rothe, J., Lesslauer, W., Lotsher, H., Land, Y., Koebel, P., Kontgen, F., Althage, A., Zinkernagel, R., Steinmetz, M., and H. Bluethmann. 1993; Mice lacking the tumour necrosis factor receptor 1 are resistant to TNF mediated toxicity but highly susceptible to infection by *Listeria monocytogenes. Nature* 364:798–802). All cell types specifically bound TNFα and expressed the 55 and 75 kDa TNFα receptors. The results presented here suggest that the anti-viral activity of TNFα was probably mediated by critical events that occur after TNFα receptor occupancy. Furthermore, both lung epithelial and CV1 cells responded to IFN-β to restrict RSV replication suggesting that TNFα and IFN-β can operate through separate and distinct pathways to restrict virus consistent with recent studies (Guidotti, L. G., Guilhot, S., and F. V. Chisari. 1994. Interleukin-2 and alpha/beta interferon down-regulate hepatitis B virus gene expression in vivo by tumor necrosis factor dependent and -independent pathways. *J. of Virol* 68:1265–1270).

TNFα can restrict virus by interfering with infection, causing cytostasis or cytolysis, or induction of genes that disrupt virus replication (Wong, G. H. W., Kamb, A., and D. V. Goeddel.1993. Antiviral properties of TNF. In B. Beutler, editor. Tumor Necrosis Factors: The Molecules and Their Emerging Role in Medicine.Raven Press. Ltd, New York, 371–381). rTNFα mediated a minor, but significant ($P<0.05$), reduction in infection of lung epithelial cells, but only at low RSV doses. At higher RSV doses, TNFα did not appear to effect infection, cell proliferation, cellular protein levels, membrane integrity, or viability in either mock or RSV infected cells but demonstrated a marked dose-dependent reduction in RSV replication.

TNFα can induce some cell types to activate TNFα/IFN-β responsive genes and can interact synergistically with IFN-β to restrict both DNA and RNA viruses (Sen, G. C., and R. M. Ransohoff. 1993. Interferon-induced antiviral actions and their regulation. *Adv. Virus Res.* 42:57–101; Wong, G. H. W., Kamb, A., and D. V. Goeddel.1993. Antiviral properties of TNF. In B. Beutler, editor. Tumor Necrosis Factors: The Molecules and Their Emerging Role in Medicine.Raven Press. Ltd, New York, 371–381). From the results presented here, it was evident that TNFα potently restricted RSV replication in all lung epithelial cells in a dose dependent manner and, at submaximal doses, interacted with low doses of IFN-β to essentially abort RSV replication in A549 cells. This interaction appeared additive rather than synergistic with RSV infected A549 cells.

TNFα and IFN-β can induce several anti-viral enzyme pathways including the 2', 5'A dependent RNase L to degrade viral mRNA; the double-stranded RNA-activated p68 kinase which can interfere with initiation of protein translation; as well as genes whose enzymatic activities have not been defined including the IFN-78K gene which is the human equivalent of the Murine Mx gene and the ISGF2 gene (Sen, G. C., and R. M. Ransohoff. 1993. Interferon-induced antiviral actions and their regulation. *Adv. Virus Res.* 42:57–101; Wong, G. H. W., Kamb, A., and Goeddel, D. V. 1993. Antiviral properties of TNF. In B. Beutler, editor. Tumor Necrosis Factors: The Molecules and Their Emerging Role in Medicine.Raven Press. Ltd, New York, 371–381). RNase L or activated P68 kinase should yield decreased cellular protein levels and eventual loss of cell viability. Lung epithelial cells demonstrated no detectable change in membrane permeability or cellular viability at 24 h post-treatment with these cytokines in both uninfected and RSV infected cells. However, recent work by the applicants indicates the IFN and TNFα increase RNase L levels in both human alveolar macrophages and lung epithelial cells suggesting this pathway may be critical in restricting RSV replication in humanlung cells. (Panuska, J. R., Rebert, N. A., Hoffmann, S. I. Anti-Respiratory Syncytial Virus Pathways in Cytokine Treated Human Lung Cells. *Am. J. of Resp. and Crit. Care Medicine* 151:A122).

Applicants further observed that TNFα, or other RSV induced products, may have a role in restricting RSV transmission between lung epithelial cells and alveolar macrophages. Lung epithelial cells were competent to transmit RSV to uninfected alveolar macrophages. In contrast, RSV infected alveolar macrophages did not transmit RSV to uninfected lung epithelium. RSV infected alveolar macrophages neither produce defective interfering virus not inactivate infectious virus (Cirino, N. M., Panuska, J. R., Villani, A., Taraf, H., Rebert, N. A., Merolla, R., Tsivitse, P., and I. A. Gilbert. 1993. Restricted replication of respiratory syncytial virus in human alveolar macrophages. *J. Gen. Virol.* 74:1527–1537) making it unlikely that these mechanisms could account for the restricted RSV transmission.

Alveolar macrophages do release low amounts of infectious RSV while simultaneously producing TNF (Panuska, J. R., Midulla, F., Cirino, N. M., Villani, A., Gilbert, I. A., McFadden, E. R., and Y. T. Huang. 1990. Virus-induced alterations in macrophage production of tumor necrosis factor and prostaglandin $E_2$. *Am. J. Physiol* (*Lung Cell Mol Physiol*) 259:L396–L402). It is possible, that TNFα renders lung epithelial cells resistant to the low doses of virus produced in these co-cultures. Addition of neutralizing antibodies to TNFα did not induce transmission of RSV from alveolar macrophages to epithelial cells. However, this result does not preclude the possibility that TNFα was active in protected areas, i.e. adherent sites, sequestered from the neutralizing antibody.

It is also possible that other molecules produced by alveolar macrophages render epithelial cells resistant to RSV. Although applicants do not yet understand the mechanism of uni-directional transmission of RSV from lung epithelial cells to alveolar macrophages, these results do suggest that virus spread through the airways does not occur by carriage of virus by alveolar macrophages but probably results from cell-cell transmission between epithelial cells. Further studies to define which pathways serve to restrict RSV transmission from alveolar macrophages to lung epithelial cells are currently being investigated.

The interaction between TNFα and IFN-β to restrict RSV has a number of physiological and clinical implications. For example, TNFα is expressed by alveolar macrophages in vivo in children naturally infected with RSV. Although TNFα can induce lung injury in animal models, the results presented herein suggest that this cytokine restricts RSV replication locally. Indeed, murine studies have shown that local production of TNF markedly restricts replication of vaccinia virus (Sambhi, S. K., Kohonen-Corish, M. R. J., and l. A. Ramshaw. 1991. Local production of tumor necrosis factor encoded by recombinant vaccinia virus is effective in controlling viral replication in vivo. *Proc Natl Acad Sci.* 88:40254029).

RSV is a poor inducing agent for IFN (Hall, C. B., Douglas, R. G. Jr, Simons, R. L., and J. M. Geiman.1978. Interferon production in children with respiratory syncytial, influenza, and parainfluenza virus infections. *J. Pediatr.* 93:28–32; Roberts, N. J. Jr, Hiscon, J., and D. J. Signs. 1992. The limited role of the interferon system response to respiratory syncytial virus challenge: analysis and comparison to influenza virus challenge. *Microbial Pathogenesis*.12:409414.) but recent studies have shown that IFN can be delivered by aerosol to volunteers to activate IFN responsive genes without inducing detectable changes in pulmonary functions or biopsies (Jaffe, H. A., Buhl, R., Mastrangeli, A., Holrody, K. J., Saltini, C., Czerski, D., Jaffe, H. S., Kramer, S., Sherwin, S., and R. G. Crystal. 1991. Organ specific cytokine therapy. *J. Clin. Invest* 88:297–302; Martin, R. J., Boguniewicz, M., Henson, J. E., Celniker, A. C., Williams, M., Giorno, R. C., and D. Y. M. Leung. 1992. The effects of inhaled interferon gamma in normal human airways. *Am. Rev. Respir. Dis.* 148:1677–1682; Halme, M., Maasilta, P., Mattson, K., Cantell, K. 1994. Pharmacokinetics and Toxicity of Inhaled Human Natural Interferon-Beta in Patients With Lung Cancer. *Respiration* 61:105–107). Furthermore, systemically administered IFN enhances clinical improvement in RSV infected children (Sung, R. Y. T., Yin, J., Oppenheimer, S. J., Tam, J. S., and J. Lau. 1993. Treatment of respiratory syncytial virus infection with recombinant interferon alfa-2a. *Arch Dis. Child* 69:440–442).

Consequently, by combining exogenous, nebulized IFN-β to the airways coupled with endogenous TNFα produced by resident alveolar macrophages, significant therapeutic benefits can be achieved in RSV infected hosts. The present invention is directed to these findings.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What we claimed is:

1. A method for treating respiratory syncytial virus (RSV) comprising administering a therapeutically effective amount of interferon-β (IFN-β) to lung epithelial cells harboring RSV.

2. The method of claim 1, wherein said interferon-β (IFN-β) is recombinant interferon-β.

3. The method of claim 1, wherein said interferon-β (IFN-β) is natural interferon-β.

4. The method of claim 3, wherein said natural interferon-β is human interferon-β.

5. The method of claim 1, wherein said lung epithelial cells harboring RSV are human lung epithelial cells.

6. A method for treating respiratory syncytial virus (RSV) comprising administering a therapeutically effective amount of interferon-β (IFN-β) to the lungs of a host suffering from RSV via respiratory tract inhalation.

7. The method of claim 6, wherein said interferon-β (IFN-β) is a nebulized solution of interferon-β (IFN-β).

8. The method of claim 6, wherein said interferon-β (IFN-β) is recombinant interferon-β.

9. The method of claim 6, wherein said interferon-β (IFN-β) is natural interferon-β.

10. The method of claim 9, wherein said natural interferon-β is human interferon-β.

11. The method of claim 6, wherein said lung epithelial cells harboring RSV are human lung epithelial cells.

12. A method of eliciting a pharmacological effect on lung epithelial cells harboring respiratory syncytial virus (RSV) comprising the step of administering a therapeutically effective amount of interferon-β (IFN-β) to said cells.

13. The method of claim 12, wherein said interferon-β (IFN-β) is recombinant interferon-β.

14. The method of claim 12, wherein said interferon-β (IFN-β) is natural interferon-β.

15. The method of claim 14, wherein said natural interferon-β is human interferon-β.

16. The method of claim 12, wherein said lung epithelial cells harboring RSV are human lung epithelial cells.

* * * * *